United States Patent

Lambert et al.

(10) Patent No.: US 12,257,103 B2
(45) Date of Patent: Mar. 25, 2025

(54) METHOD AND SYSTEM FOR NON-INVASIVELY CHARACTERIZING A HETEROGENEOUS MEDIUM USING ULTRASOUND

(71) Applicants: SUPERSONIC IMAGINE, Aix-en-Provence (FR); CENTRE NATIONAL DE LA RECHERCHE SCIENTIFIQUE—CNRS, Paris (FR); Ecole Supérieure de Physique et de Chimie Industrielles de la Ville de Paris, Paris (FR)

(72) Inventors: William Lambert, Ivry sur Seine (FR); Alexandre Aubry, Ivry sur Seine (FR); Mathias Fink, Meudon (FR); Laura Cobus, Winnipeg (CA)

(73) Assignees: SUPERSONIC IMAGINE, Aix-en-Provence (FR); CENTRE NATIONAL DE LA RECHERCHE SCIENTIFIQUE - CNRS, Paris (FR); Ecole Superieure de Physique et de Chimie Industrielles de la Ville de Paris, Paris (FR)

( * ) Notice: Subject to any disclaimer, the term of this patent is extended or adjusted under 35 U.S.C. 154(b) by 302 days.

(21) Appl. No.: 17/631,929

(22) PCT Filed: Jul. 31, 2020

(86) PCT No.: PCT/FR2020/051416
§ 371 (c)(1),
(2) Date: Feb. 1, 2022

(87) PCT Pub. No.: WO2021/023933
PCT Pub. Date: Feb. 11, 2021

(65) Prior Publication Data
US 2024/0032889 A1 Feb. 1, 2024

(30) Foreign Application Priority Data

Aug. 2, 2019 (FR) ........................... 1908904

(51) Int. Cl.
A61B 8/08 (2006.01)
A61B 8/00 (2006.01)
G01S 15/88 (2006.01)

(52) U.S. Cl.
CPC .......... *A61B 8/0833* (2013.01); *A61B 8/4488* (2013.01); *A61B 8/5207* (2013.01); *G01S 15/88* (2013.01)

(58) Field of Classification Search
None
See application file for complete search history.

(56) References Cited

U.S. PATENT DOCUMENTS 4,817,614 A 4/1989 Hassler et al.
5,720,289 A 2/1998 Wright et al.
(Continued)

FOREIGN PATENT DOCUMENTS

CN 102481142 A 5/2012
CN 103969651 A 8/2014
(Continued)

OTHER PUBLICATIONS

International Search Report and Written Opinion of the International Searching Authority for International Patent Application No. PCT/FR2020/051416 mailed Jan. 27, 2021, 12 pages.
(Continued)

*Primary Examiner* — Isam A Alsomiri
*Assistant Examiner* — Jonathan D Armstrong
(74) *Attorney, Agent, or Firm* — Merchant & Gould P.C.

(57) ABSTRACT

Method for non-invasively characterizing a heterogeneous medium using ultrasound, comprising a step of generating a
(Continued)

series of incident ultrasonic waves, a step of recording an experimental reflection matrix $R_{ui}(t)$ defined between the input emission basis (i) and an output reception basis (u), a step of determining a response $REP(r,\Delta r)$ of the medium between an input virtual transducer ($TV_{in}$) calculated based on an input focusing of the experimental reflection matrix that creates an input focal spot around a first point (P1), and an output virtual transducer ($TV_{out}$) calculated based on an output focusing of the experimental reflection matrix that creates an output focal spot around a second point (P2), said response being expressed as a function of a central point (PC) of spatial position (r) in the medium located midway between the first and second points (P1, P2).

19 Claims, 10 Drawing Sheets

(56) References Cited

U.S. PATENT DOCUMENTS

| | | | |
|---|---|---|---|
| 7,403,879 B2 * | 7/2008 | Placko | G06F 30/23 |
| | | | 703/2 |
| 7,460,963 B2 * | 12/2008 | Lemistre | A61N 2/00 |
| | | | 324/754.29 |
| 2009/0234230 A1 | 9/2009 | Bercoff et al. | |
| 2011/0125014 A1 | 5/2011 | Derode et al. | |
| 2015/0182195 A1 * | 7/2015 | Liu | A61B 8/4477 |
| | | | 600/459 |
| 2015/0196283 A1 | 7/2015 | Yamamoto | |
| 2018/0199918 A1 | 7/2018 | Tsushima | |
| 2021/0310787 A1 * | 10/2021 | Aubry | G01N 21/4795 |
| 2022/0003721 A1 * | 1/2022 | Aubry | G01N 29/46 |
| 2022/0082527 A1 * | 3/2022 | Lambert | G01N 29/024 |
| 2022/0082529 A1 * | 3/2022 | Lambert | G01S 7/52049 |
| 2022/0082693 A1 * | 3/2022 | Lambert | A61B 8/54 |
| 2022/0084496 A1 * | 3/2022 | Lambert | G01N 29/46 |
| 2023/0160854 A1 * | 5/2023 | Brutt | G01N 29/38 |
| | | | 73/628 |
| 2024/0036004 A1 * | 2/2024 | Lambert | G01N 29/032 |
| 2024/0042488 A1 * | 2/2024 | Yamada | H04R 17/00 |
| 2024/0260931 A1 * | 8/2024 | Kato | A61B 3/16 |

FOREIGN PATENT DOCUMENTS

| | | | | |
|---|---|---|---|---|
| FR | 3099580 A1 * | 2/2021 | | A61B 8/0833 |
| JP | 2014079568 A | 5/2014 | | |
| WO | 0232316 A1 | 4/2002 | | |
| WO | 2010/001027 A1 | 1/2010 | | |
| WO | 2020/016250 A1 | 1/2020 | | |

OTHER PUBLICATIONS

French Search Report for French Patent Application No. 1908904 mailed Apr. 2, 2020, 2 pages.
Mallart, R. et al., "The van Cittert-Zernike theorem in pulse echo measurements", J. Acoust. Soc. Am., 90(5): 2718-2727 (1991).
Montaldo, G. et al., "Coherent Plane-Wave Compounding for Very High Frame Rate Ultrasonography and Transient Elastography", IEEE Transactions on Ultrasonics, Ferroelectrics, and Frequency Control, 56(3): 489-506 (2009).
Japanese Office Action and Written Opinion issued in related patent application No. 2022500603, on Feb. 13, 2024.
Japanese Office Action and Search Report issued in related patent application No. 2022500603, on Apr. 1, 2024.

* cited by examiner

METHOD AND SYSTEM FOR NON-INVASIVELY CHARACTERIZING A HETEROGENEOUS MEDIUM USING ULTRASOUND

This application is a National Stage Application of PCT/FR2020/051416, filed 31 Jul. 2020, which claims benefit of French Patent Application Serial No. FR 1908904, filed 2 Aug. 2019, and which applications are incorporated herein by reference. To the extent appropriate, a claim of priority is made to each of the above disclosed applications.

TECHNICAL FIELD

The present description relates to methods and systems for non-invasive ultrasonic characterization of a heterogeneous medium, and applies in particular to medical imaging or to non-destructive testing and more generally to all areas in which ultrasound imaging can be used.

PRIOR ART

In the field of acoustic imaging, the goal is to characterize a completely or partially unknown medium, by actively probing it using ultrasonic waves. In particular, this is the principle of the ultrasound machine used in medical imaging.

The resolution of an acoustic imaging system can be defined as the ability to discern the small details of an object. In principle, an acoustic imaging system is limited by diffraction, and the theoretical resolution is given by $\lambda/2$ (where $\lambda$ is the wavelength of sound in the medium), or by the finite angle of aperture of the detector. In practice, however, the resolution is often degraded by variations in the speed of sound in the propagation medium.

In fact, most of the time in acoustic imaging, the medium is considered to be homogeneous, with a constant speed of sound c0. However, the assumption of a homogeneous environment does not always apply. For example, in the case of an ultrasound of the liver, the probe is placed between the patient's ribs. The acoustic waves travel through successive layers of fat and muscle before reaching the target organ. The soft tissues each have different mechanical properties. The speed of sound is therefore far from homogeneous, between 1450 m/s for adipose tissue and 1600 m/s for the liver. The variations in the speed of sound cause a different phase shift in the waves, depending on the locations through which they are propagating. This results in an aberration of the acoustic wavefront, which leads to a distortion of the resulting ultrasound image and therefore to a degradation of its resolution and its contrast. These aberrations can be such that they compromise the results of the medical examination.

As illustrated in FIGS. 1A-1C, conventional ultrasound methods use an array 10 of piezoelectric transducers 11 which can emit and receive ultrasonic pulses independently. The position of each transducer is identified by the vector u. When such an array is placed facing a medium that one wishes to study, the medium can be insonified and imaged in various ways.

A first way to generate an ultrasound image of the medium to be studied is to emit an ultrasonic pulse from one of the transducers of the array whose position is identified by the vector $u_{in}$ (FIG. 1A, left diagram). This results in a divergent cylindrical (or spherical) incident wave for a 1D (or 2D) array of transducers. This wave is reflected by the scatterers 21 of the medium 20 and the backscattered field is recorded as a function of time by each of the transducers 11 (FIG. 1A, right diagram). By repeating this operation with each transducer successively used as a source, the set of impulse responses $R(u_{out}, u_{in}, t)$ between each transducer is measured, where the vector $u_{out}$ denotes the position of the detector. These responses form the reflection matrix $R_{uu}(t)$ expressed in the basis of the transducers. The advantage of such a measurement lies in the fact that this matrix contains all the information about the analyzed medium, it then being possible to apply a set of matrix operations to it for the purposes of imaging the medium, for example. On the other hand, such acquisition assumes that the medium remains fixed for the duration of the measurements, which can be very difficult in the case of in-vivo use. In addition, the energy emitted by a single piezoelectric element is low, which can result in a poor signal-to-noise ratio.

Other methods are known for generating an image of the medium to be analyzed, in which focused emissions are carried out using a beamforming technique. As shown in FIG. 1B, left diagram, these methods consist of applying to the transducers 11 a set of appropriate delays, based on a homogeneous speed model, in order to correct the travel times of the waves so that all the pulses arrive together at the target focal point at position $r_{in}$. Due to the physical limitations of diffraction, the ultrasound is concentrated in a region bounded by the aperture of the ultrasound probe. In order to construct an ultrasound image, a focusing step is also performed at reception. The set of echoes captured by the elements 11 of the array 10 are then processed to simulate the effect of a lens at reception, as described in FIG. 1B, right diagram. The signals received by the transducers are time-shifted to bring them back into phase. These delays are identical to those applied at emission. In the emission phase, all signals interfere at the point of position $r_{in}$. At reception, the signals coming from this same point $r_{out}=r_{in}$ interfere electronically by summation of the signals at ballistic time $t=2\|u_{out}-r_{in}\|/c$. This summation gives the final result of the focusing at reception. The method illustrated in FIG. 1B, known as the confocal method with double focusing at emission and at reception, makes it possible to directly image the reflectivity of the medium with a lateral resolution limited by diffraction, an excellent axial resolution only limited by the duration of the initial pulse, and excellent contrast. However, this method is time-consuming because it requires physically focusing at emission at each of the points of the medium or at least at a depth, in each of the rows of the image.

Another imaging technique, developed more recently, consists of generating an image of the medium by insonifying the medium with a series of plane waves. FIG. 1C illustrates the principle of this so-called plane-wave ultrasound, described for example in the article by G. Montaldo et al. *"Coherent plane-wave compounding for very high frame rate ultrasonography and transient elastography"* (IEEE Trans. Ultrason., Ferroelect. Freq. Control 56 489-506, 2009). Delays are applied to each signal at emission (FIG. 1C, left diagram) to form a wavefront inclined at an angle $\theta_{in}$ relative to the array of transducers 10. At reception (FIG. 1C, right diagram), the field backscattered by the medium, $R(u_{out}, \theta_{in}, t)$, is measured by all the position sensors $u_{out}$ for a series of incident plane waves in which the angle of incidence $\theta_{in}$ is varied. The set of these responses forms a reflection matrix $R_{u\theta}(t)$ defined between the Fourier basis (or plane-wave basis) as input and the basis of the transducers as output. Once this matrix is recorded, the signals are time-shifted before being coherently summed in order to focus the data digitally at emission and at reception for each point of position $r_{in}$. The number of captures necessary to form an ultrasound image is reduced compared to standard ultrasound (focused emissions), for the same level of contrast and resolution of the ultrasound image.

FIG. 2 illustrates the influence of aberrations in the medium on conventional ultrasound imaging methods (FIGS. 1A to 1C). The delays initially determined and to be applied to each transducer of the array at emission and at reception are not optimal for evaluating an image of the medium, since they are determined under the assumption of a homogeneous medium with a constant speed of sound. An aberrating layer 22 induces distortion of the incident wavefront. At emission or excitation, step 25, the delay rules used do not allow the acoustic energy to be concentrated in the region bounded by the diffraction limits, regions conventionally called the focal spot. At reception, in step 26, the delay rules used do not allow correctly selecting the ultrasonic signals originating from the focal point of the medium, and intermix the signals originating from an equally aberrant focal spot. This results in a double aberration in the image construction process, which greatly degrades its resolution. New delay rules can then be recalculated in order to compensate for the effect of the aberrating layer by adding an additional delay rule to the delays generally used in beamforming.

However, these aberration corrections do not completely correct either these aberrations or the degradation of the resolution. There is a need to better estimate the focus quality in the medium.

The document "*The van Cittert-Zernike theorem in pulse echo measurements*", (Raoul Mallart and Mathias Fink, J. Acoust. Soc. Am. 90 (5), November 1991) studied the statistical properties of the field reflected by a random medium in a single scattering regime. In particular, it was demonstrated that, for a focused incident wave, the spatial covariance of the reflected field is proportional, from the far field, to the Fourier transform of the transmitting aperture function. In other words, this theorem explains that the study of the statistical properties of the reflected field in the far field makes it possible to determine the focus quality of the incident wave in the medium.

However, this approach only provides a general and average estimate of the resolution of an ultrasound image, because it requires statistically averaging the correlations of the reflected field over a large number of implementations of the disorder, i.e. over a large number of focal points of the incident wave. It does not allow obtaining a precise and local assessment of the focus quality at each point of the image. Moreover, this approach is only valid in a single scattering regime.

Patent application WO-2010/001027 proposes a method for ultrasonic probing capable of separating the multiple scattering component from the single scattering component by filtering a frequency transfer matrix representative of the responses between the transducers of the set of transducers. This method makes it possible to obtain information on the multiple scattering in which the reflected wave results from several successive reflections on scatterers, and for which the time-of-flight is not directly related to the distance between a scatterer and the transducers.

However, this approach only allows obtaining the depth-wise evolution of the multiple scattering and single scattering intensities. It does not allow access to the lateral variations of these numbers and therefore does not allow access, for each point of the image, to the ratio between the multiple scattering and single scattering intensities. Thus, only average information about the reliability of the ultrasound image at each depth can be obtained, based on the fact that single scattering is predominant.

It is therefore necessary to propose a method which overcomes each of the above disadvantages.

SUMMARY

According to a first aspect, this description relates to a method for non-invasive ultrasonic characterization of a heterogeneous medium, the method comprising:

a step of generating a series of incident ultrasonic waves in a region of the heterogeneous medium generated by means of transducers, said series of incident ultrasonic waves constituting an emission basis (i);

a step of recording an experimental reflection matrix IWO defined between the input emission basis (i) and an output reception basis (u);

a step of determining a response REP(r,Δr) of the medium between an input virtual transducer ($TV_{in}$) of spatial position $r_{in}$ calculated based on an input focusing of the experimental reflection matrix corresponding to an input focal spot around a first point (P1) and an output virtual transducer ($TV_{out}$) of spatial position $r_{out}$ calculated based on an output focusing of the experimental reflection matrix corresponding to an output focal spot around a second point (P2), said response being expressed as a function of a central point (PC) of spatial position r in the medium, said central point (PC) being located midway between the first and second points (P1, P2) and being the origin of a measurement axis ($AX_m$) passing through said first and second point, said measurement axis forming an angle β relative to a first axis (X) of the medium, and the first point (P1) being at a distance coordinate +Δr on the measurement axis, and the second point (P2) being at a distance coordinate −Δr on the measurement axis.

By means of these arrangements, the method makes it possible, in a highly advantageous manner, to probe the medium very locally in any direction of the measurement axis passing through the first point and the second point, in order to determine, by the input and output foci, a new matrix of local responses REP(r,Δr) (very rich in local information) at any point in the medium of position r and for any angular direction β of analysis.

This method then advantageously makes it possible to define characteristic parameters which give local information about the medium, parameters which are very useful for quantifying the quality of the ultrasound image, and which can be used to optimize these images by computation without having to iterate through new emissions and/or captures, which is an important advantage during in vivo measurements.

The recorded experimental reflection matrix $R_{ui}(t)$ can be a "real" matrix, i.e. composed of real coefficients in the time domain, with the electrical signals recorded by each of the transducers being real numbers. Alternatively, this matrix can be a "complex" matrix, i.e. composed of complex values, for example in the case of demodulation for in-phase/quadrature beamforming (known as "IQ beamforming").

In various embodiments of the method according to this disclosure, use may optionally be made of one or more of the following arrangements.

According to one aspect, in the step of determining the response REP(r,Δr), the input focusing of the experimental reflection matrix uses an outward time-of-flight of the waves between the emission basis and the input virtual transducer; the output focusing uses a return time-of-flight of the waves between the output virtual transducer and the reception basis.

According to one aspect, the response REP(r,Δr) of the medium is calculated by the following formula:

$$REP(r, \Delta r) = \frac{1}{N_{in}N_{out}} \sum_{i_{in}} \sum_{u_{out}} R_{ui}(u_{out}, i_{in}, \tau(r_{in}, r_{out}, u_{out}, i_{in}))$$

in which
$N_{in}$ is the number of elements of the emission basis i,
$N_{out}$ is the number of elements of the output reception basis u,
$R_{ui}(t)$ is the experimental reflection matrix, in which $R_{ui}(u_{out}, i_{in}, \tau(r_{in}, r_{out}, u_{out}, i_{in}))$ is the element of the experimental reflection matrix $R_{ui}(t)$ recorded by transducer $u_{out}$ consecutive to emission $i_{in}$ at time τ,
τ is a time which is the sum of the outward time-of-flight $\tau_{in}$ of the ultrasonic wave between the emission basis i and the first point P1 and the return time-of-flight $\tau_{out}$ of the ultrasonic wave between the second point P2 and the reception basis u, as explained by the following formula:

$$\tau(r_{in}, r_{out}, u_{out}, i_{in}) = \tau_{in}(r_{in}, i_{in}) + \tau_{out}(r_{out}, u_{out})$$

According to one aspect, the method further comprises:
a step of determining a response profile PR(δr) which is a plurality of responses REP(r,Δr) calculated for a plurality of values of the distance coordinate Δr and for the same central point (PC), and for a same measurement axis ($AX_m$), corresponding to a predetermined angle β, δr being the distance of the second point from the central point, i.e. the value such that Δr=δr·$u_β$, $u_β$ being a unit vector in the direction of the measurement axis $AX_m$ defined by the angle β.

According to one aspect, the method further comprises:
a step of determining the resolution w(r) of the central point (PC) based on a modulus of the response profile, in which the resolution w(r) is a width of the peak of said modulus of the response profile PR(δr), centered around the zero distance coordinate (|Δr|=0).

According to one aspect of the method, the width of the peak is estimated at a height which is a portion of the maximum height of said peak, said portion being for example half the maximum height of the peak.

According to one aspect, the method further comprises:
a step of determining a focusing criterion F(r) of the central point (PC) based on the resolution w(r) and a theoretical resolution $w_0(r)$, said theoretical resolution $w_0(r)$ being determined based on the input emission basis (i) and the output reception basis (u).

According to one aspect, the method further comprises:
an image optimization step in which the focusing criterion F(r) is calculated at a plurality of points of the medium, and at least one calculation parameter for the input focusing and/or output focusing is optimized by minimizing or maximizing a mean of said focusing criterion F(r) for said plurality of points.

According to one aspect of the method, said at least one calculation parameter comprises the speed of sound in the medium.

According to one aspect of the method, the theoretical resolution is determined by a technique comprised in the following list:

a first analytical calculation at the central point (PC), for a pulse ($\omega_1$) and the emission basis (i) and the reception basis (u), in which the theoretical resolution is calculated by the angle from which the transducer array is viewed from the central point (PC),
a second analytical calculation at the central point (PC), for a pulse range (Δω) and the emission basis (i) and the reception basis (u), in which the theoretical resolution is an integral calculation over said pulse range of the angle from which the transducer array is viewed from the central point (PC) weighted by the frequency spectrum of signals from the experimental reflection matrix $R_{ui}(t)$, and
a third calculation of a wave propagation simulation, firstly between the first point of the medium corresponding to an input virtual transducer ($TV_{in}$) and the emission basis (i), and secondly between the second point of the medium corresponding to an output virtual transducer ($TV_{out}$) and the reception basis (u), said simulation using the response REP(r,Δr) and a model of wave propagation in the medium.

According to one aspect, the method further comprises:
a step of determining a level of symmetry α(r) which is the mean correlation coefficient between two reciprocal responses, said mean being calculated for distance coordinate values of modulus greater than a predetermined resolution $w_d(r)$ and/or being calculated for a range of angle values β or for a predetermined angle value $β_d$,
a first response REP1(r,Δr) of the medium between an input virtual transducer ($TV_{in}$) of spatial position $r_{in}$ calculated based on an input focusing of the experimental reflection matrix corresponding to an input focal spot around a first point (P1) and an output virtual transducer ($TV_{out}$) of spatial position $r_{out}$ calculated based on an output focusing of the experimental reflection matrix corresponding to an output focal spot around a second point (P2), and
a second response REP2(r, −Δr) of the medium between an input virtual transducer ($TV_{in}$) of spatial position $r_{in}$ calculated based on an input focusing of the experimental reflection matrix corresponding to an input focal spot around the second point (P2) and an output virtual transducer ($TV_{out}$) of spatial position $r_{out}$ calculated based on an output focusing of the experimental reflection matrix corresponding to an output focal spot around the first point (P1).

According to one aspect of the method, the level of symmetry is calculated by the following formula:

$$\alpha(r) = \frac{\langle REP1(r, \Delta r) \cdot REP2(r, -\Delta r)^* \rangle_{(|\Delta r| > w_d(r,\beta),\beta)}}{\sqrt{\langle |REP1(r, \Delta r)|^2 \rangle \langle |REP2(r, -\Delta r)|^2 \rangle}}$$

or by the following formula:

$$\alpha(r) = \frac{\langle \text{Re}[REP1(r, \Delta r) \cdot REP2(r, -\Delta r)^*] \rangle_{(|\Delta r| > w_d(r,\beta),\beta)}}{\sqrt{\langle |REP1(r, \Delta r)|^2 \rangle \langle |REP2(r, -\Delta r)|^2 \rangle}}$$

in which
Re[·] is the real part mathematical operator,
|·| is the modulus mathematical operator,
<·> is the mean mathematical operator, and
* is the complex conjugation operator.

According to one aspect, the method further comprises:
a step of determining a first multiple scattering indicator ε(r) which is calculated by:

$$\epsilon(r) = \frac{\alpha(r)}{1 - \alpha(r)}$$

α(r) being the level of symmetry defined at the central point (PC) of the medium.

According to one aspect, the method further comprises:
a step of determining an afocal intensity $I_{off}(r)$ which is the mean of a squared modulus of the responses REP(r,Δr), the mean being calculated for distance values of modulus greater than a predetermined resolution $w_d(r)$ and/or being calculated for a range of angle values β or for a predetermined angle value $β_d$, for example calculated by the following formula:

$$I_{off}(r) = \langle I(r,\Delta r) \rangle_{(|\Delta r| > w_d(r))}$$

a step of determining a multiple scattering intensity $I_M(r)$ which is the product of the level of symmetry α(r) and the afocal intensity $I_{off}(r)$, i.e.:

$$I_M(r) = \alpha(r) \cdot I_{off}(r)$$

a step of determining a noise intensity $I_N(r)$ which is the product of one minus the level of symmetry α(r) and the afocal intensity $I_{off}(r)$, i.e.:

$$I_N(r) = (1 - \alpha(r)) \cdot I_{off}(r)$$

such that we have the following relation:

$$I_{off}(r) = I_M(r) + I_N(r)$$

According to one aspect of the method, the first multiple scattering indicator ε(r) is calculated by a ratio between the multiple scattering intensity $I_M(r)$ and the noise intensity $I_N(r)$, i.e.:

$$\epsilon(r) = \frac{I_M(r)}{I_N(r)}$$

According to one aspect, the method further comprises:
a step of determining a confocal intensity $I_{on}(r)$ which is the value of a squared modulus of the response REP(r, |Δr|=0) for a distance coordinate value of zero (|Δr|=0), i.e. for a point of the medium for which the first point (P1), the second point (P2), and the central point (PC) are coincident,
a step of determining a single scattering intensity $I_S(r)$ calculated based on the following equation:

$$I_{on}(r) = I_S(r) + 2I_M(r) + I_N(r)$$

According to one aspect, the method further comprises:
a step of determining a second multiple scattering indicator γ(r) which is calculated by:

$$\gamma(r) = \frac{I_M(r)}{I_S(r)}$$

According to one aspect, the method further comprises:
a step of determining an image of a local characterization parameter of the medium, said local characterization parameter being determined based on the response REP(r,Δr).

According to one aspect of the method, the local characterization parameter is selected from a list comprising the resolution w(r), the focusing criterion F(r), the level of symmetry α(r), the first multiple scattering indicator ε(r), the second multiple scattering indicator γ(r), the afocal intensity $I_{off}(r)$, the confocal intensity $I_{on}(r)$, the multiple scattering intensity $I_M(r)$, the single scattering intensity $I_S(r)$, the noise intensity $I_N(r)$.

According to a second aspect, this description relates to a system for non-invasive ultrasonic characterization of a heterogeneous medium, configured to implement all the examples of ultrasonic characterization methods as described above. The system for ultrasonic characterization according to the second aspect comprises:
a first array (10) of transducers suitable for generating a series of incident ultrasonic waves in a region of the heterogeneous medium, said series of incident ultrasonic waves constituting an emission basis (i), and suitable for recording as a function of time the ultrasonic waves backscattered by said region; and
a computing unit (42) coupled to the first array of transducers and suitable for:
recording an experimental reflection matrix $R_{ui}(t)$ defined between the input emission basis (i) and an output reception basis (u);
determining a response REP(r,Δr) of the medium between an input virtual transducer ($TV_{in}$) of spatial position $r_{in}$ calculated based on an input focusing of the experimental reflection matrix corresponding to an input focal spot around a first point (P1) and an output virtual transducer ($TV_{out}$) of spatial position $r_{out}$ calculated based on an output focusing of the experimental reflection matrix corresponding to an output focal spot around a second point (P2), said response being expressed as a function of a central point (PC) of spatial position r in the medium, said central point (PC) being located midway between the first and second points (P1, P2) and being the origin of a measurement axis ($AX_m$) passing through said first and second point, said measurement axis forming an angle β relative to a first axis (X) of the medium, and the first point (P1) being at a distance coordinate +Δr on the measurement axis, and the second point (P2) being at a distance coordinate −Δr on the measurement axis.

The system for characterization according to this description may comprise at least one array of transducers which are both emitter and receiver, or several arrays of transducers, some dedicated to emission, others to reception of ultrasonic waves.

BRIEF DESCRIPTION OF FIGURES

Other features and advantages of the technique presented above will be apparent from reading the detailed description below, presented in a non-limiting manner for illustrative purposes, made with reference to the figures in which.

In the various embodiments which will be described with reference to the figures, similar or identical elements bear the same references.

DETAILED DESCRIPTION

In the following detailed description, only certain embodiments are described in detail to ensure clarity of the description, but these examples are not intended to limit the general scope of the principles that emerge from this description.

The various embodiments and aspects described in this description can be combined or simplified in multiple ways. In particular, the steps of the various methods can be repeated, inverted, and/or executed in parallel, unless otherwise specified.

Certain elements depicted in the specification and claims are denoted in bold, meaning these elements are vectors. A person of ordinary skill in the art would recognize the context in which the following elements are used, and would understand that these elements represent vectors, even if said elements are not depicted in bold in every instance in the publication of the present application, or in any patent that may issue therefrom. These elements include, but are not necessarily limited to:

$R_{ui}$ (e.g., as used in the context of "experimental reflection matrix $R_{ui}(t)$")

i (e.g., as used in the context of "input emission basis (i)", as well as in $i_{in}$);

u (e.g., as used in the context of "output reception basis (u)", as well as in $u_{out}$);

r (e.g., as used in the context of "spatial positions r, $r_{in}$, and $r_{out}$");

Δr (e.g., as used in the context of "distance coordinates +Δr and −Δr"); and $u_β$ (e.g., as used in the context of "δr·$u_β$").

Figure 3:
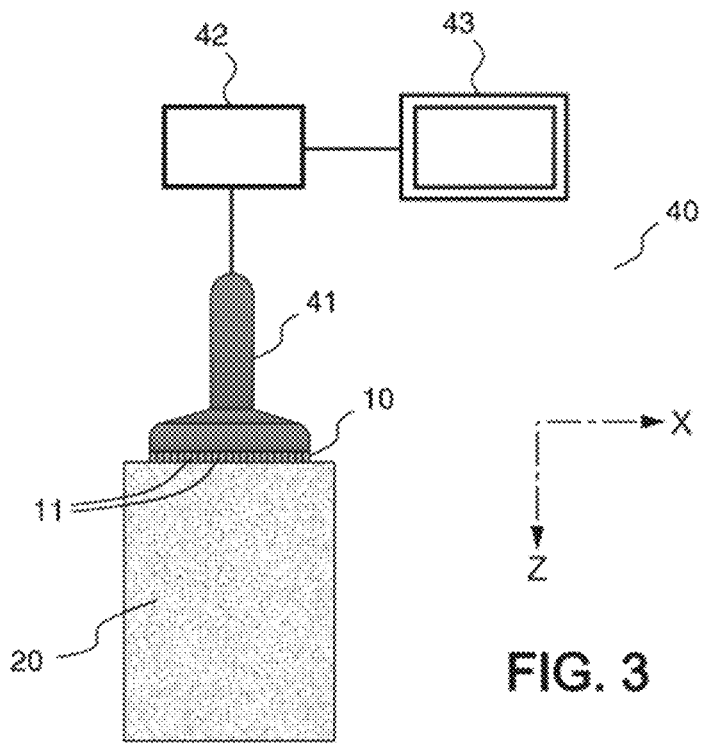
FIG. 3 illustrates an example of a system for ultrasonic characterization, for implementing the methods for ultrasonic characterization according to this description.

FIG. 3 illustrates an example of a system 40 for ultrasonic characterization, for implementing methods for ultrasonic characterization of a heterogeneous medium 20, according to this description. The system 40 comprises at least a first array 10 of transducers 11, for example a linear or two-dimensional array; the transducers are for example piezoelectric ultrasonic transducers which may be in the conventional form of a rigid bar placed in contact with the medium 20. The array of transducers is, for example, part of a probing device 41, hereinafter also referred to by the more common term "probe"; the array of transducers is connected to a computing unit 42, which itself may be connected to a display device 43; the computing unit transmits and records electrical signals to/from each of the transducers 11. The ultrasonic transducers then convert these electrical signals into ultrasonic waves and vice versa. "Connection" or "link" between the probing device 41, the computing unit 42, and the display device 43, is understood to mean any type of wired connection of the electrical or optical type, or any type of wireless connection using any protocol such as WiFi, Bluetooth, or others. These connections or links are one-way or two-way.

The computing unit 42 is configured to implement calculation or processing steps, in particular to implement the steps of methods according to this description. By convention, a spatial reference system of the medium 20 is defined by taking a first axis X and a second axis Z perpendicular to the first. For simplicity, the first axis X corresponds to the direction in which the transducers 11 are aligned for a linear array, and the second axis Z corresponds to the depth of the medium 20 relative to this array 10 of transducers 11. This definition can be extended to a three-axis spatial reference system in the case of a two-dimensional array.

In FIG. 3, as in the rest of the description, reference is made to an array of transducers for emission and reception, it being understood that, in a more general case, several arrays of transducers could be used simultaneously. They can be both transmitter and receiver, or only a transmitter for some and only a receiver for others.

When reference is made in this description to calculation or processing steps, in particular for implementing steps of the methods, it is understood that each calculation or processing step can be implemented by software, hardware, firmware, microcode, or any suitable combination of these technologies. When software is used, each calculation or processing step may be implemented by computer program instructions or software code. These instructions may be stored in or transmitted to a storage medium readable by a computer (or computing unit) and/or executed by a computer (or computing unit) in order to implement these calculation or processing steps.

Defining the Analysis of a Point of the Medium

This description describes methods and systems for non-invasive ultrasonic characterization of a heterogeneous sample. These methods and systems are based on definitions shown in FIG. 4: a central point PC of spatial position r is defined in the spatial reference system of the medium, and located midway between a first point P1 and a second point P2. A measurement axis $AX_m$ is defined, passing through the first point P1 and the second point P2, and forming an angle β with the first axis X of the array of transducers 11. The central point PC is located on the origin of the measurement axis $AX_m$ (distance coordinate of zero on the measurement axis). The first point P1 is at a distance coordinate −Δr and the second point P2 is at a distance coordinate +Δr from the central point PC, origin of the measurement axis.

The spatial position r and the distance coordinate Δr are denoted in bold, meaning that these elements are vectors of the position and offset relative to a position, vectors in the spatial reference system of the medium (X,Z). The distance coordinate vector Δr thus takes into account the direction of the measurement axis $AX_m$, and its angle β relative to the first axis X. Other definitions of the positions of points relative to other points are possible and accessible to any specialist in the field of ultrasound. In particular, the first and second points can be identified by a distance |Δr| and the angle β, or by another position identifier.

These two points P1 and P2 can be at a short distance from each other, i.e. a few millimeters from each other, and for example 20 millimeters or less.

Figure 4:
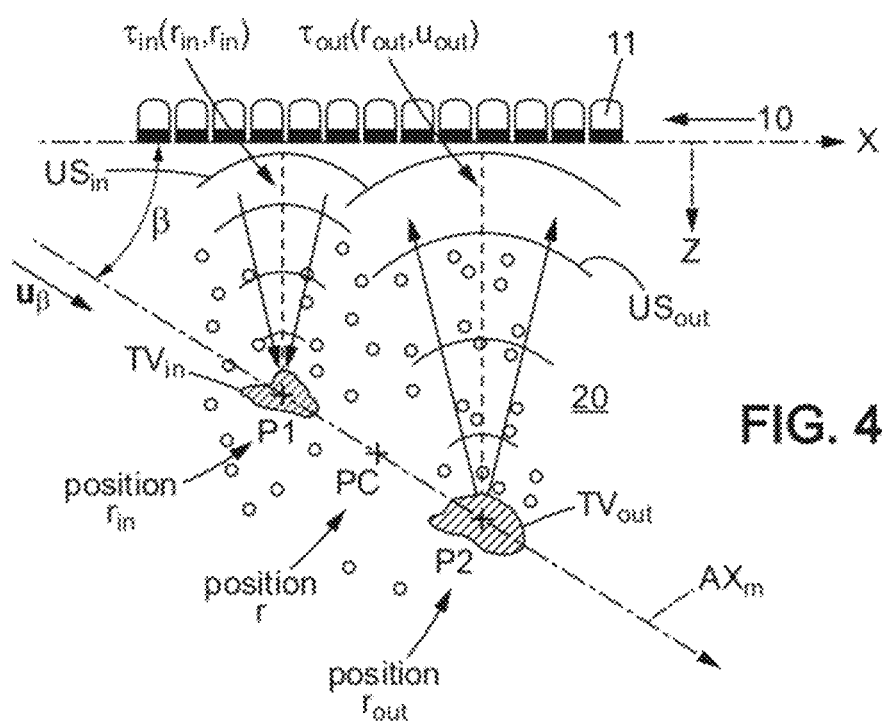
FIG. 4 illustrates the definitions used in the method for ultrasonic characterization according to this description.

As shown in FIG. 4, the method for non-invasive ultrasound characterization comprises:
- a step of generating a series of incident ultrasonic waves $US_{in}$ in a region of said heterogeneous medium, by means of an array 10 of transducers 11, said series of incident ultrasonic waves being an emission basis i; and
- a step of recording an experimental reflection matrix $R_{ui}(t)$ defined between the input emission basis i and an output reception basis u;
- a step of determining a response REP(r,Δr) of the medium between an input virtual transducer $TV_{in}$ of spatial position $r_{in}$ at the first point P1 and an output virtual transducer $TV_{out}$ of spatial position $r_{out}$ at the second point P2, said response being expressed as a function of the central point PC of spatial position r.

As the central point PC is midway between the two points P1, P2, we have the following relations:

$$r=(r_{out}+r_{in})/2 \text{ and } \Delta r=(r_{out}-r_{in})/2$$

Figure 1A:
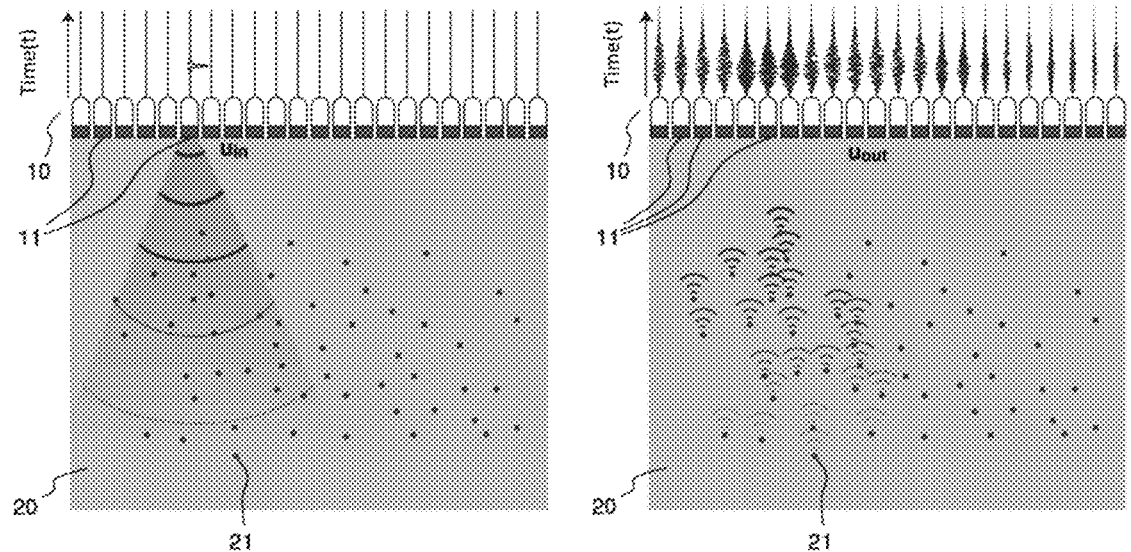
FIGS. 1A to 1C (already described) illustrate known emission/reception mechanisms for ultrasound imaging and quantification.
Figure 1B:
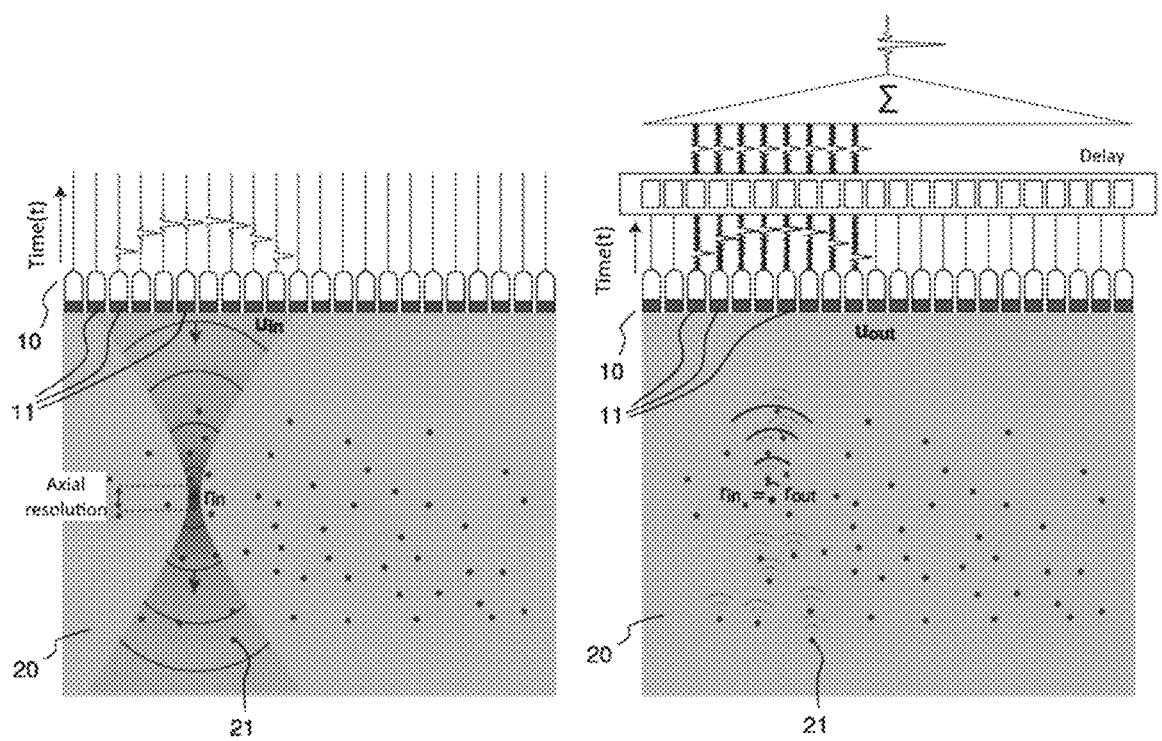
Figure 1C:
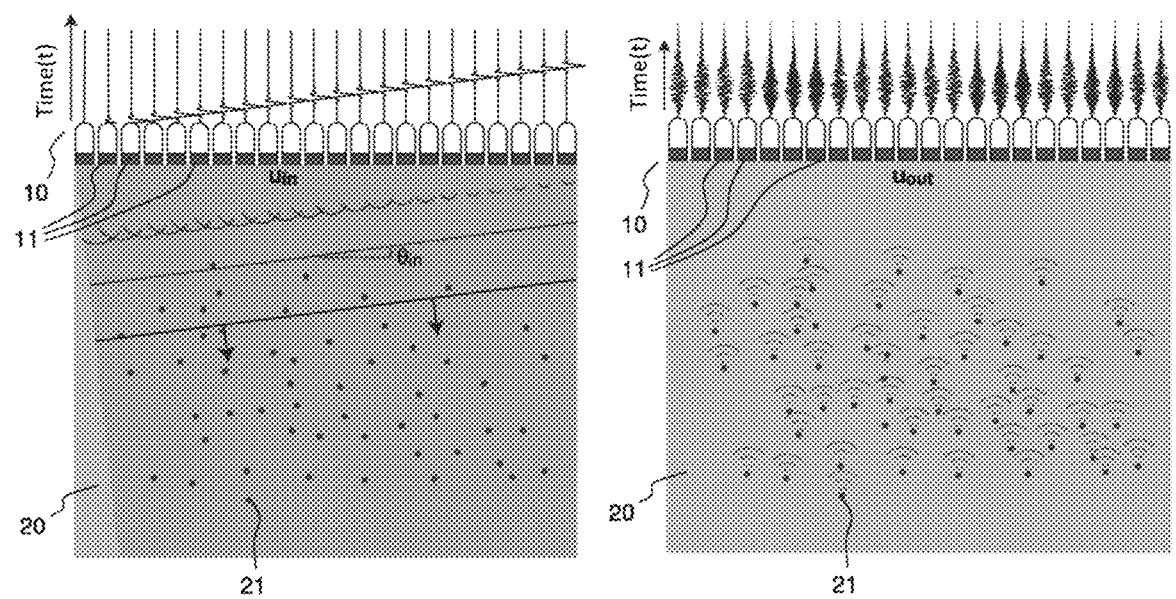
Figure 2:
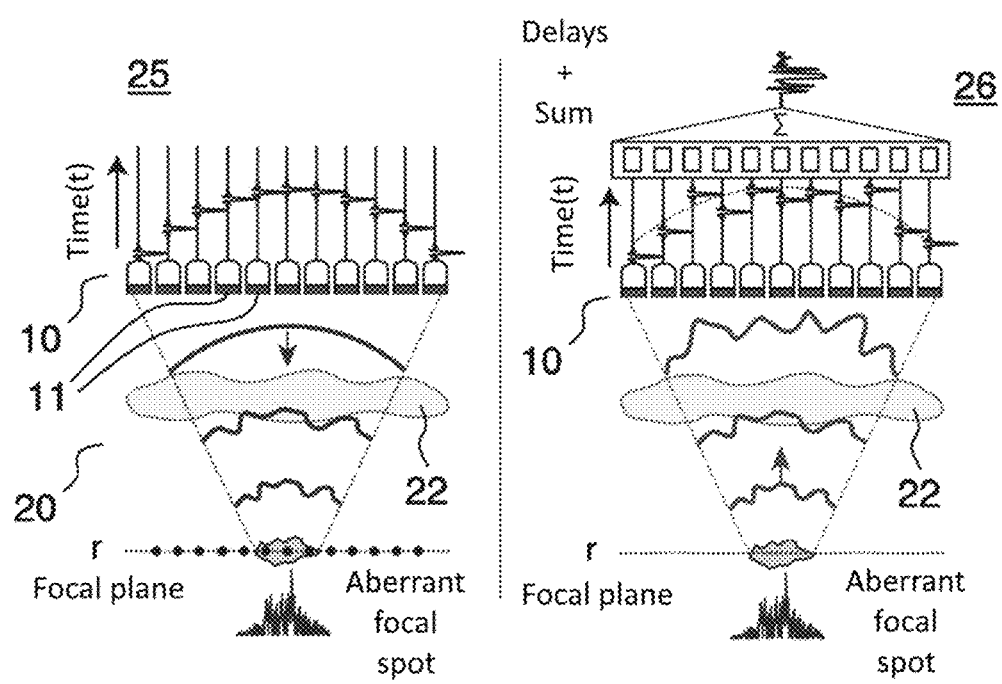
FIG. 2 (already described) illustrates the impact of aberrations in ultrasound imaging according to the prior art.

The input emission basis i being for example a basis of waves each generated by one of the transducers 11 of the array 10 or a basis of plane waves of angular inclination θ with respect to the axis X, as described above in the description of FIGS. 1A to 1C.

The reception basis u is usually the basis of the transducers 11.

Thus, the step of generating ultrasonic waves is understood to be between the emission basis i and the reception basis u. This ultrasonic generation step is therefore defined for any type of ultrasonic wave of the focused or unfocused type, such as plane waves.

In the recording step, the experimental reflection matrix $R_{ui}(t)$ is therefore defined between the input emission basis i and an output reception basis u. This matrix contains all the temporal responses of the medium, measured at time t by each transducer 11 of spatial coordinate $u_{out}$ for each emission $i_{in}$. It is understood that the elements named with the index "in" refer to emission (i.e. the input) and the elements named with the index "out" refer to reception (i.e. the output).

In the step of determining a response REP(r,Δr), we apply:
- an input focusing process based on the experimental reflection matrix $R_{ui}(t)$ that creates an input focal spot around the first point P1, said input focal spot corresponding to the input virtual transducer $TV_{in}$, and
- an output focusing process based on the experimental reflection matrix $R_{ui}(t)$ that creates an output focal spot around the second point P2, said output focal spot corresponding to the output virtual transducer $TV_{out}$.

The input focusing process uses an outward time-of-flight of the waves between the emission basis (i) and the input virtual transducer $TV_{in}$. The output focusing process uses a return time-of-flight of the waves between the output virtual transducer $TV_{out}$ and the transducers of the reception basis (u). These input and output focusing processes in fact form an input-output focusing process, hereinafter referred to as the focusing process.

The first point P1 being relative to the input virtual transducer $TV_{in}$, it is therefore located at a coordinate −Δr on the measurement axis $AX_m$ in relation to the central point PC, and the second point P2 being relative to the output virtual transducer $TV_{out}$, it is therefore located at a coordinate +Δr on the measurement axis $AX_m$ in relation to the central point PC.

The input focusing (at emission) is configured to concentrate the acoustic wave around point P1 over a spatial extent corresponding to the input focal spot. The scatterers located inside this region in the medium then generate a wave which is backscattered towards the probe. This region, characterized by the focal spot at emission and the reflectivity of the corresponding medium is called the input virtual transducer $TV_{in}$ and can be interpreted as a "virtual" source.

The output focusing (at reception) is configured to select the echoes generated by scatterers located around point P2 over a spatial extent corresponding to the output focal spot. This region, characterized by the output focal spot (reception) and the reflectivity of the corresponding medium is called the output virtual transducer $TV_{out}$ and can be interpreted as a "virtual sensor".

The response REP(r,Δr) can therefore be interpreted as an estimate of the pressure field coming from position $r_{out}$ for a focusing at position $r_{in}$.

In other words, in this method of non-invasive ultrasonic characterization, the input virtual transducer $TV_{in}$ corresponds to an ultrasonic "virtual source" at spatial position $r_{in}$ in the medium and the output virtual transducer $TV_{out}$ corresponds to an ultrasonic "virtual sensor" at spatial position $r_{out}$. Thus, the method is able to probe the medium around point P1 and/or point P2, spatially, which makes it possible to obtain new information about the propagation of the waves.

For example, a calculation of the response REP(r,Δr) of the medium between the input virtual transducer $TV_{in}$ and the output virtual transducer $TV_{out}$ by a focusing process, which is for example an improved beamforming method, which can be expressed by the following simplified formula:

$$REP(r, \Delta r) = \frac{1}{N_{in}N_{out}} \sum_{i_{in}} \sum_{u_{out}} R_{ui}(u_{out}, i_{in}, \tau(r_{in}, r_{out}, u_{out}, i_{in})) \quad \text{(Eq. 1)}$$

in which
- $N_{in}$ is the number of elements of the emission basis i,
- $N_{out}$ is the number of elements of the output reception basis u,
- $R_{ui}(t)$ is the experimental reflection matrix, in which $R_{ui}(u_{out}, i_{in}, \tau(r_{in}, r_{out}, u_{out}, i_{in}))$ is the element of the experimental reflection matrix $R_{ui}(t)$ recorded by transducer $u_{out}$ consecutive to emission $i_{in}$ at time τ.

The time τ is the sum of the outward time-of-flight $\tau_{in}$ of the ultrasonic wave between the transducers of the emission basis i and the first point P1 and the return time-of-flight $\tau_{out}$ of the ultrasonic wave between the second point P2 and the transducers of the reception basis u, as explained by the following formula:

$$\tau(r_{in}, r_{out}, u_{out}, i_{in}) = \tau_{in}(r_{in}, i_{in}) + \tau_{out}(r_{out}, u_{out}) \quad \text{(Eq. 2)}$$

The times-of-flight $\tau_{in}$ and $\tau_{out}$ are calculated based on a speed of sound model. The hypothesis consists of considering a homogeneous medium with a constant speed of sound $c_0$. In this case, the times-of-flight are obtained directly, based on the distances between the probe and the virtual transducers.

The number of elements of the emission basis $N_{in}$ is for example greater than or equal to two. The number of elements of the reception basis $N_{out}$ is for example greater than or equal to two.

This improved beamforming formula is therefore a double summation of the temporal responses recorded in the experimental reflection matrix $R_{ui}$: a first summation linked to the input focusing (emission) according to emission basis i at point P1 of position spatial $r_{in}$, and a second summation related to the output focusing (reception) according to reception basis u at point P2 of spatial position $r_{out}$. This calculation is therefore carried out for the spatial coordinates of the two points P1 and P2 (of spatial positions $r_{in}$, $r_{out}$). The result of this improved beamforming formula is therefore a time signal which is a pressure field for these two spatial coordinates ($r_{in}$, $r_{out}$).

Note that the particular case of calculating a response REP(r, $\Delta r$=0) corresponds to the situation in which the points P1 and P2 are coincident at the same spatial position $r_{in}$=$r_{out}$=r. This configuration corresponds exactly to the case of the usual confocal ultrasound imaging in which each pixel of the image results from a process of input focusing (at emission) and output focusing (at reception) at a same point in the medium, and for the points of images of the medium. The time-of-flight τ then corresponds to the outward and return time-of-flight required for a wave to propagate from the probe to the single point of spatial position r, then from this point r to each transducer of the probe.

By means of these arrangements, the method makes it possible to probe the medium very locally in any direction corresponding to the measurement axis $AX_m$, in order to extract, via the input and output focusing, more local information about the medium at the central point PC of spatial position r, between the first point and second point of the heterogeneous medium 20. This local information is entirely contained within the values of the calculated response, the response REP(r,$\Delta r$) of the medium which can be used to characterize each point of the medium, for example in terms of resolution or in terms of multiple scattering. This local information is entirely contained within the values of the calculated temporal response which can be exploited to characterize each point of the medium.

Indeed, it is customary to deduce, from this temporal response after beamforming, an estimate of the reflectivity of the medium by considering the absolute value of the confocal signals characterized by the superposition of points P1 and P2, i.e. the superposition of the focal spots of the input and output virtual transducers (i.e. $r_{in}$=$r_{out}$ and |$\Delta r$|=0). This reflectivity then corresponds to the value of a pixel of a conventional ultrasound-type image.

The responses REP(r,$\Delta r$) can thus be determined for any set of real distance values |$\Delta r$|, for example between two limits such as $-\Delta r_{max}$ and $+\Delta r_{max}$, these limits being determined so that the input and output virtual transducers remain inside the medium 20. (|$\Delta r$|, β) are then the polar coordinates of the distance coordinates vector $\Delta r$.

In this previous convention of spatial description around the central point PC of spatial position r, the response REP(r, $-\Delta r$) corresponds to inverting the spatial positions of the input and output virtual transducers.

The set of responses REP(r,$\Delta r$) can then be recorded in a matrix of the same name. This matrix of responses is a focused reflection matrix, which records a pressure field calculated at any point in the medium with the defined hypotheses.

One therefore obtains a response matrix REP(r,$\Delta r$) (4-dimensional in the case of a linear probe, including two for r and $\Delta r$) which records focused time signals.

Figure 5:
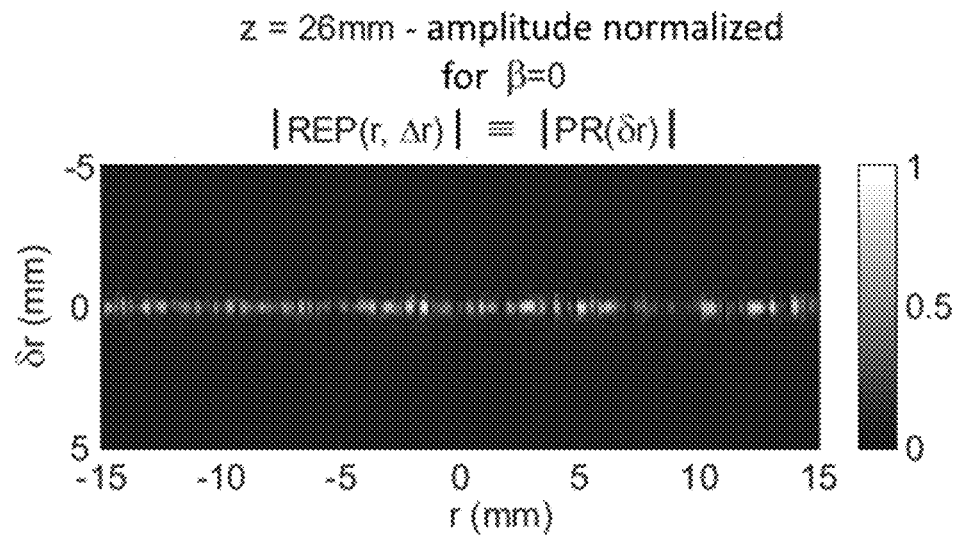
FIG. 5 illustrates an example image representing the modulus of a response matrix REP(r,Δr) according to the method for ultrasonic characterization as in FIG. 4.

FIG. 5 shows an image corresponding to a sub-matrix of the response matrix REP, said sub-matrix corresponding to a set of several central points PC of spatial position r in which the Z axis coordinate is fixed, and the angle β is zero. Thus, in this image the abscissa corresponds to a variation along the X axis of the position of the central point PC and the ordinate corresponds to the distance coordinate $\Delta r$ relative to this central point. The values of the points of this image (response) not on the abscissa axis of this image have a low (but not zero) value. The values of the points of this image (response) on the abscissa axis have a value corresponding to the intensity of the ultrasonic image point at the central point PC.

Such an image can be extracted from the response REP (r,$\Delta r$) for variations in distance coordinates $\Delta r$ on a single measurement axis AXm or several measurement axes, i.e. for one or more angle values β.

A polar image representing the variation of the modulus of the response as a function of the separation distance |$\Delta r$| and of the angle β can also be constructed, which gives a representation of the variation of the response around a central point PC, and therefore of the focal spot at this point.

Calculating a Response Profile PR(δr)

Having obtained the responses of the medium determined according to the above method, a step of determining a response profile PR(δr) can be carried out, the response profile being a plurality of responses REP(r,$\Delta r$) calculated for a plurality of values of the distance coordinate $\Delta r$. This response profile PR(δr) is considered for a same central point PC of spatial position r and along a same measurement axis $AX_m$, corresponding to a same direction of angle β. The response profile PR(δr) is therefore determined for a plurality of distances δr, the distance δr being the abscissa of the second point P2 with respect to the central point PC, i.e. the value such that $\Delta r = \delta r \cdot u_\beta$, $u_\beta$ being a unit vector in the direction of the measurement axis $AX_m$ defined by the angle β. In other words, the response profile PR(δr) is a vertical slice of the image of FIG. 5, and this response profile is the curve of said image slice.

The responses REP(r,$\Delta r$) can be complex values, particularly when using a focusing formulation in complex values, as is known in in-phase/quadrature beamforming (known as "IQ beamforming"). Consequently, the response profile PR(δr) can also be represented by any modulus of these complex responses.

Figure 6:
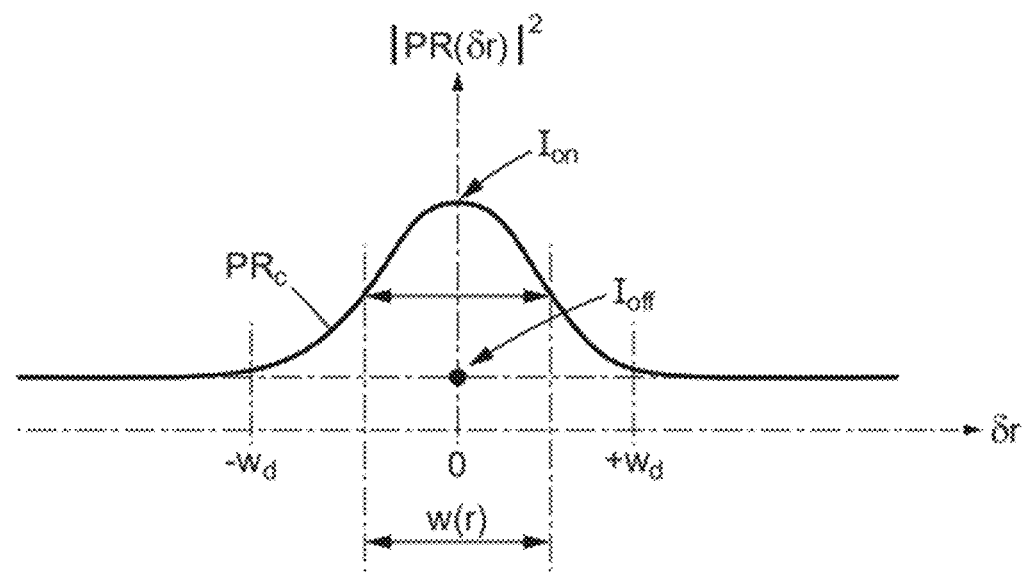
FIG. 6 illustrates an example response profile PR(δr) corresponding to the response matrix of FIG. 5.

FIG. 6 shows a schematic example of the squared modulus of a response profile PR(δr) that can be determined for a central point PC of the medium and for a direction of angle β: here for β=0 because the image of FIG. 5 is also established for this angle value.

However, the angle β can take any value between zero (0) and pi (π), and therefore a response profile curve $PR_c$ can be plotted or determined for multiple angle values β.

The set of response profiles PR(δr) or PR(δr, β) (if several angles are used, but in the following we will only keep the spatial position for the sake of simplifying the description) or PR(r, δr, β) (if also using the spatial position of the central point) can be recorded in a matrix of the same name.

The response profile PR(δr) presents:
- an over-intensity (maximum of the curve) for a low value of δr which corresponds to a single scattering in which the width is related to the focal spot, and an incoherent background present for all values of δr, which is due to echoes arising from the multiple scattering phenomenon and noise.

The sub-matrix represented in FIG. 5 is therefore the set of response profiles PR(δr) for a set of central points PC of spatial position r in which the Z axis coordinate is fixed, and the angle β is zero (or constant).

This response profile PR(δr) is a basic representation making it possible to determine new parameters for the local characterization of the medium and/or for the performance of the ultrasound imaging process (i.e. beamforming). We will illustrate the results of these characterization parameters by images of the heterogeneous medium, constructed with said characterization parameters.

Figure 7:
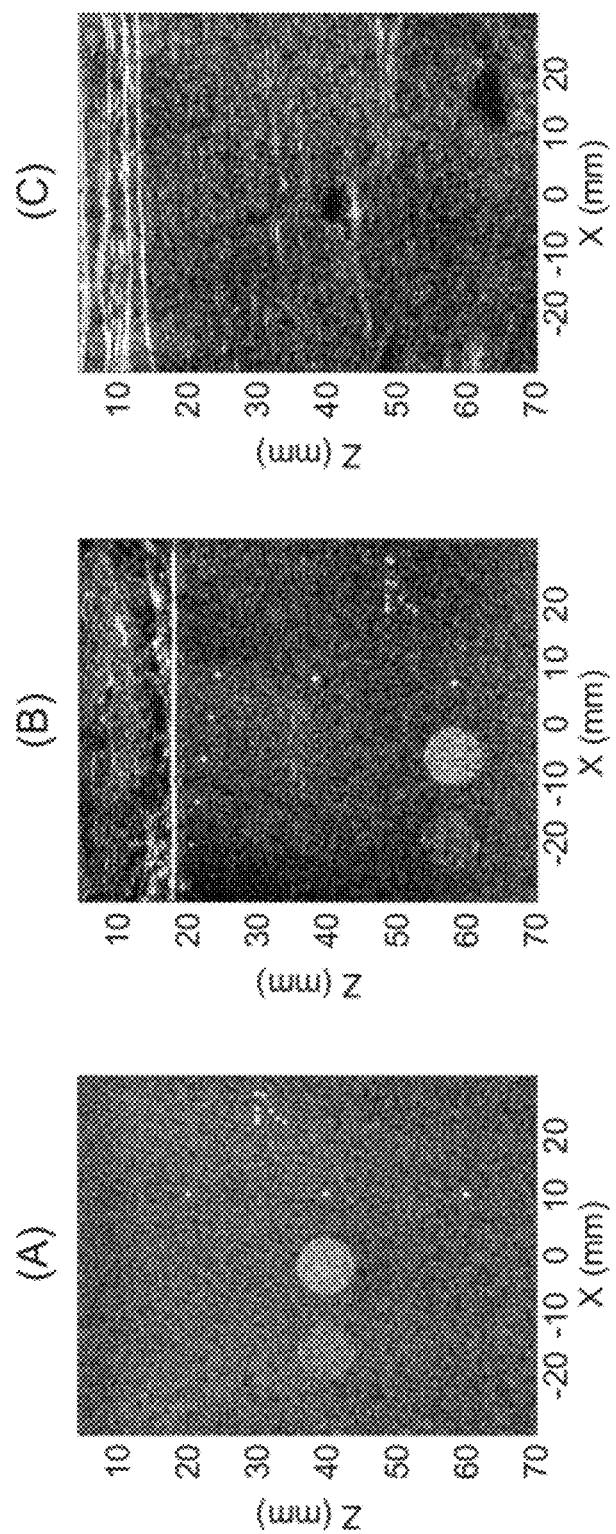
FIG. 7 illustrates ultrasound images of three heterogeneous media, part A of this figure corresponding to a test medium referred to as "phantom", part B of this figure corresponding to a medium having a layer of meat placed on the test medium, and part C of this figure corresponding to a medium which is an "in vivo" liver.

These characterization parameters for three different cases of heterogeneous media are described in more detail below. FIG. 7 shows ultrasound images of these three heterogeneous media:

in part A of this FIG. 7 (on the left), one can see an image of a test medium (medium A) referred to as "phantom", which includes two cylinders of differing rigidity, in part B of this FIG. 7 (in the center), one can see an image of a medium having a layer of meat placed on the above test medium (medium B), and in part C of FIG. 7 (on the right), one can see an image of a medium which is an "in vivo" liver (medium C).

Calculating the Resolution of Point w(r)

A step of determining the resolution $w(r)$ of the central point PC in the direction of the measurement axis $AX_m$ of angle β can then be performed, based on a modulus of the response profile. This resolution is therefore a local estimate of the resolution of the ultrasound image.

Note that the modulus of the response profile as shown in FIG. 6 comprises a peak or maximum around the zero distance coordinate Δr (|Δr|=0). This peak or over-intensity of the response profile is linked to the single scattering echoes and appears when the focal spots of the two virtual transducers $TV_{in}$ and $TV_{out}$ overlap. The spatial extent of this peak is therefore strongly correlated with the spatial dimensions of the input and output focal spots along the direction of angle β and therefore with the local resolution of the ultrasound image.

The resolution w(r) can then be determined for example by the width of this peak. The width of this peak is for example determined at a height which is a portion of the maximum height of this peak. For example, the portion of the height will be one-half or one-third (⅓) or two-thirds (⅔) or any other ratio of the maximum height. The maximum height of the peak is in fact the intensity of the ultrasound image at the central point PC if one considers only the squared modulus of the response profile, i.e. |PR(δr=0)|², as is the case in the example illustrated in FIG. 6.

It is understood that the resolution depends on the central point PC considered, but also on the angle β.

Therefore, the proposed method makes it possible to obtain at each point:

the axial resolution for an angle β of π/2, i.e. by the value w(r) taken for a response profile corresponding to an angle β=π/2, and the lateral resolution for a zero angle β, i.e. by the value w(r) taken for a response profile corresponding to an angle β=0.

The method makes it possible to define, at any point in the medium, the extent of the focal spot and therefore the resolution of the ultrasound method in each of the directions of angle β.

Figure 8:
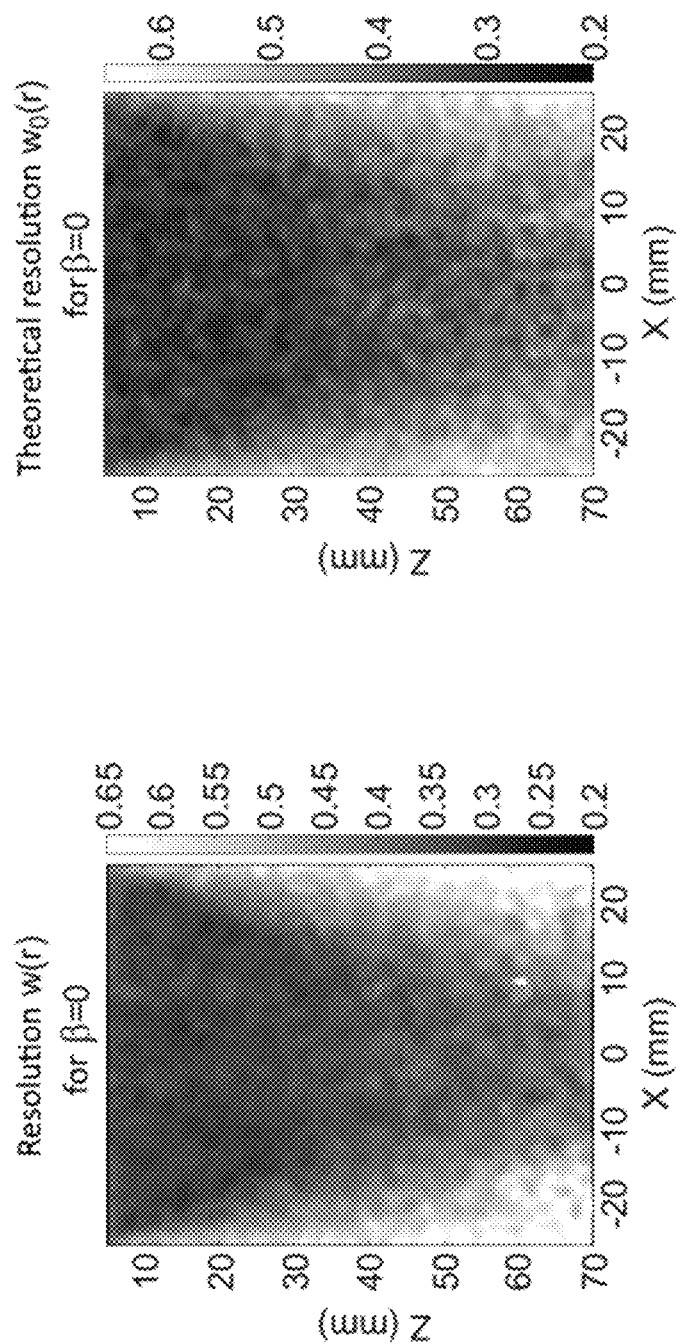
FIG. 8 illustrates an image of resolution w(r) (on the left) and an image of theoretical resolution $w_0(r)$ (on the right), established for the test medium (of part A) of FIG. 7.

The image in the left part of FIG. 8 shows an example calculation of the resolution w(r, β) at each point of the test medium (medium A). Note that the resolution degrades with depth and when moving towards the edge of the image.

Calculating the Theoretical Resolution $w_0(r)$

According to a first variant, the theoretical resolution $w_0(r)$ is determined by a first analytical calculation at the central point (PC) for a pulse ($\omega_1$), the emission basis (i), and the reception basis (u): It is calculated by the angle from which the transducer array is viewed from the central point (PC). It depends on the maximum half angle of aperture used during emission to insonify the central point of spatial position r, or during reception to collect the echoes coming from this central point.

According to a second variant, the theoretical resolution $w_0(r)$ is determined by a second analytical calculation at the central point (PC) for a pulse range (Δω) and the emission basis (i) and the reception basis (u). It is obtained by an integral calculation over said pulse range and over the angle from which the transducer array is viewed from the central point (PC) weighted by the frequency spectrum of recorded signals. The latter can be obtained by averaging the modulus of the Fourier transform of the elements of the experimental reflection matrix $R_{ui}(t)$.

According to a third variant, the theoretical resolution $w_0(r)$ is determined by a third calculation of wave propagation simulation, firstly between the first point of the medium corresponding to an input virtual transducer ($TV_{in}$) and the emission basis (i), and secondly between the second point of the medium corresponding to an output virtual transducer ($TV_{out}$) and the reception basis (u), said simulation using the response REP(r,Δr) and a model of wave propagation in the medium. This third calculation reflects the double focusing step carried out in order to calculate the response profiles PR(r, β, δr). This third simulation calculation consists of generating a theoretical reflection matrix associated with a random medium in which the speed of sound corresponds exactly to the speed of sound model assumed for calculating the responses REP(r,Δr). This simulation then uses the same emission basis and the same reception basis as those used for the physical experiment. The set of operations carried out to determine the resolution w(r) are then repeated to calculate the theoretical resolution $w_0(r)$ based on the theoretical reflection matrix generated. All the diffraction phenomena are entirely taken into account and an estimate of the theoretical resolution of the medium without aberration is thus obtained. Note that the statistical properties of the medium such as the average reflectivity of a region, the spectrum of the backscattered echoes, can be deduced from the responses REP(r,Δr) in order to use a simulation which best models the experiment performed.

The image in the right part of FIG. 8 shows an example calculation of the theoretical resolution $w_0(r)$ at each point of the test medium (medium A). Note that the resolution degrades with depth and also when moving towards the edge of the image. Note that this image is very similar to the image in the left part of this same figure. The calculation of the resolution carried out by the preceding method is therefore in agreement with the calculation of the theoretical resolution.

Calculating a Focusing Criterion F(r)

A step of determining a focusing criterion F(r) of the central point PC can then be performed, based on the resolution w(r) and a theoretical resolution $w_0(r)$. The theoretical resolution is for example determined based on an input emission basis i, an output reception basis u, and a modeling of the propagation of ultrasonic waves in the medium.

Usually, the focusing criterion F(r) is a ratio of said resolution and theoretical resolution, or the reverse (a simple rule). In other words, we can obtain:

$$F(r) = w(r)/w_0(r) \quad \text{(Eq. 3)}$$

or $$F(r) = w_0(r)/w(r) \quad \text{(Eq. 4)}$$

Figure 9:
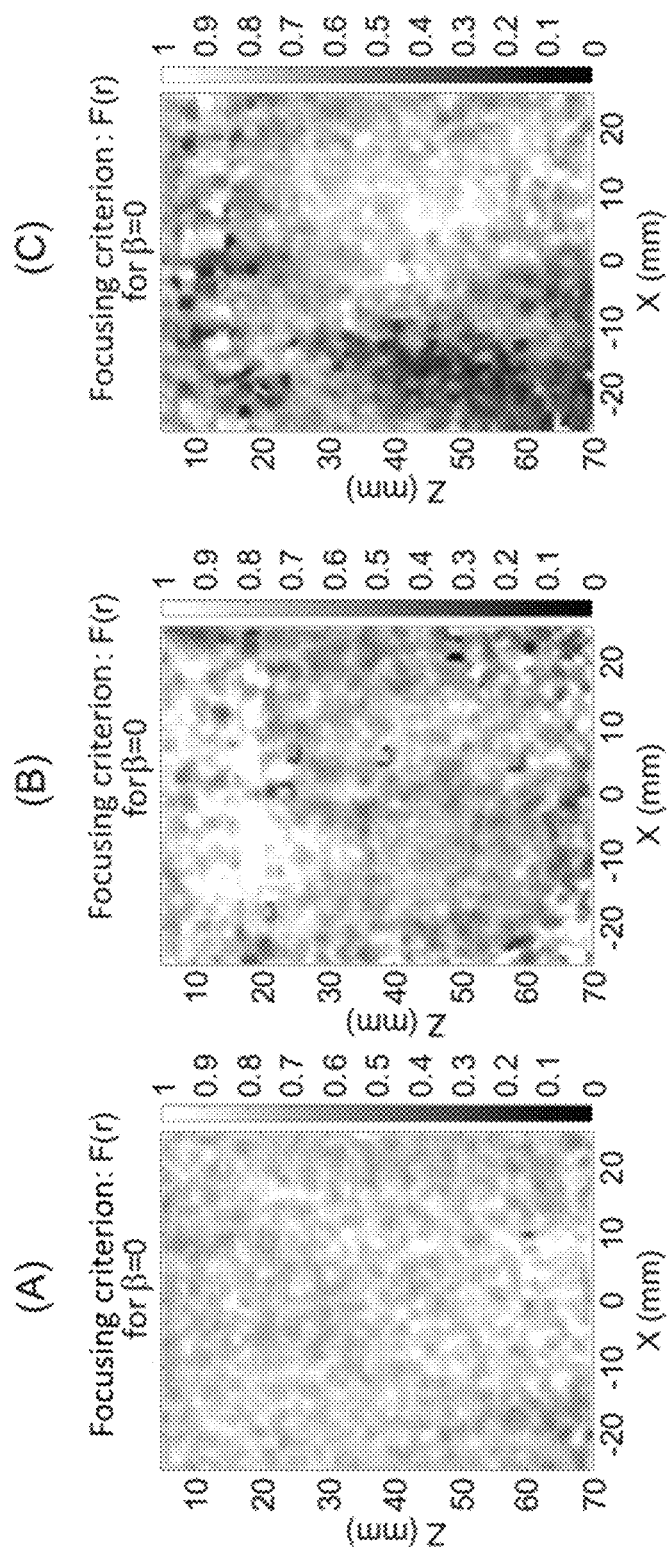
FIG. 9 illustrates images of the focusing criterion F(r), established for the three heterogeneous media of FIG. 7 (parts A, B, and C respectively)

FIG. 9 illustrates images of the focusing criterion F(r), established for the three heterogeneous media of FIG. 7 (media A, B, and C, which correspond between FIGS. 7 and 9).

A value of one (1) for this focusing criterion corresponds to an identical resolution and theoretical resolution (light in the figure). A value close to zero (0) for this focusing criterion corresponds to divergent resolution values (dark in the figure), i.e. a degraded focusing.

The image of medium A illustrates great homogeneity with a mean of this focusing criterion that is close to 0.97. This means that the ultrasound image is well formed and that the focusing assumptions are correct. The images of media B and C show notable degradations corresponding to heterogeneities located upstream of the ultrasonic wave propagation: layer of meat at the surface for medium B and adipose or muscle tissue for the liver of medium C. The image of medium C highlights very degraded regions (dark regions at the bottom left of this image) which means that the image produced in FIG. 7 (part C) also has the same problems at the same locations. Here, the image of the focusing criterion can indicate to the operator of the ultrasound system that the left part of their ultrasound image is of poor quality, especially in spatial resolution. This can help the user to interpret the ultrasound image in order to establish a diagnosis preferentially on correctly imaged regions or to modify the manner in which he or she generates said ultrasound image. For example, this can encourage the operator to modify the positioning of the probe (i.e. the array of transducers) so as to obtain a focusing criterion of good quality in the area(s) of interest for medical diagnosis.

Advantageously, the imaging system which implements the present technique will be able to superimpose an ultrasound image on an image of the focusing criterion.

Calculating a Level of Symmetry α(r)

A step of determining a level of symmetry α(r) of the central point PC can then be performed, this level of symmetry being a mean correlation coefficient between two reciprocal responses: i.e. by exchanging positions $r_{in}$ and $r_{out}$ of the input virtual transducer $TV_{in}$ and output virtual transducer $TV_{out}$. The criterion of acoustic reciprocity of the medium at the central point PC of spatial position r is thus tested. Note that the signals resulting from multiple scattering phenomena are reciprocal while those resulting from electronic noise are not correlated.

For this method, the following are determined:
- a first response REP1(r,Δr) of the medium between an input virtual transducer $TV_{in}$ (spatial position $r_{in}$) calculated based on an input focusing of the experimental reflection matrix that creates an input focal spot around the first point P1 and an output virtual transducer $TV_{out}$ (spatial position $r_{out}$) calculated based on an output focusing of the experimental reflection matrix that creates an output focal spot around the second point P2, and

- a second response EP2(r, −Δr) of the medium between an input virtual transducer $TV_{in}$ (spatial position $r_{in}$) calculated based on an input focusing of the experimental reflection matrix that creates an input focal spot around the second point P2 and an output virtual transducer $TV_{out}$ (spatial position $r_{out}$) calculated based on an output focusing of the experimental reflection matrix that creates an output focal spot around the first point P1.

In addition, the mean correlation coefficient is calculated for distance coordinate values Δr of modulus greater than a predetermined resolution $w_d(r)$ (as shown in FIG. 6) and/or being calculated for a range of angle values β or for a predetermined angle value $β_d$.

The predetermined resolution $w_d(r)$ is advantageously a value greater than half the resolution w(r). Preferably, the predetermined resolution $w_d(r)$ is a value greater than one time, two times, or three times the resolution w(r), in order to better exclude the values of the peak, as can be seen in FIG. 6. Thus, the mean correlation coefficient according to this variable indicates that the correlation coefficient is averaged for values of the distance coordinate Δr far from the peak, and therefore for virtual transducers far from the central point PC, which in effect makes it possible to test the acoustic reciprocity of this central point PC, i.e. the symmetry of the response matrix REP(r,Δr) relative to the abscissa axis (see an example of such a matrix in FIG. 5). Although the values beyond the predetermined resolution are small, comparison by a mean correlation of the symmetry allows reliably estimating a level of symmetry α(r) of the central point PC.

Advantageously, the mean correlation coefficient is calculated for a range of angle values β or for a predetermined angle value $Δ_d$. Thus, the mean correlation coefficient according to this variable indicates that the correlation coefficient is averaged for one or more angle values β, which makes it possible to test the angular symmetry or based on an angular sector the level of symmetry around the central point PC, i.e. the reciprocity of this central point PC.

Advantageously, the mean correlation coefficient is calculated for distance coordinate values Δr of modulus greater than a predetermined resolution $w_d(r)$ and for a range of angle values β. Thus, the correlation is averaged over distance coordinate values for which the single scattering contribution is zero, the latter only appearing for a modulus of the distance coordinate that is below the predetermined resolution.

This also makes it possible to obtain a more robust and stable estimate of the level of symmetry α(r).

For example, the level of symmetry α(r) can be calculated by the following correlation formula:

$$\alpha(r) = \frac{\langle REP1(r, \Delta r) \cdot REP2(r, -\Delta r)^* \rangle_{(|\Delta r| > w_d(r,\beta),\beta)}}{\sqrt{\langle |REP1(r, \Delta r)|^2 \rangle \langle |REP2(r, -\Delta r)|^2 \rangle}} \quad \text{(Eq. 5)}$$

or for example by the following correlation formula:

$$\alpha(r) = \frac{\langle \text{Re}\,[REP1(r, \Delta r) \cdot REP2(r, -\Delta r)^*] \rangle_{(|\Delta r| > w_d(r,\beta),\beta)}}{\sqrt{\langle |REP1(r, \Delta r)|^2 \rangle \langle |REP2(r, -\Delta r)|^2 \rangle}} \quad \text{(Eq. 6)}$$

in which
Re[·] is the real part mathematical operator,
|·| is the modulus mathematical operator, ⟨·⟩ is the mean mathematical operator, this operator being able to be applied according to one or more variables (in the above, for example, distance coordinate values greater than a predetermined resolution and angle values β), and

* is the complex conjugation operator.

Several correlation formulas can be used, and the specialist will modify this definition according to his or her requirements and the characteristics of the medium observed.

Generally speaking, the level of symmetry α(r) is close to zero (0) if the propagation of the ultrasonic waves does not behave reciprocally around the central point PC, and the level of symmetry α(r) is close to one (1) if the propagation of ultrasonic waves behaves symmetrically or reciprocally around the central point PC.

Thus, this level of symmetry tests the validity of the acoustic reciprocity for the portion of the signals corresponding to multiple scattering. This makes it possible to differentiate the multiple scattering from noise, as noise does not comply with the property of acoustic reciprocity.

Calculating a First Multiple Scattering Indicator ε(r)

A step of determining a first multiple scattering indicator ε(r) of the central point PC can then be performed, this multiple scattering indicator being for example calculated by the following formula:

$$\epsilon(r) = \frac{\alpha(r)}{1 - \alpha(r)} \qquad \text{(Eq. 7)}$$

in which
α(r) is the level of symmetry defined at the central point PC of the medium.

This first multiple scattering indicator ε(r) is zero if the level of symmetry is zero, and it tends towards infinity if the level of symmetry is close to one (1).

Figure 10:
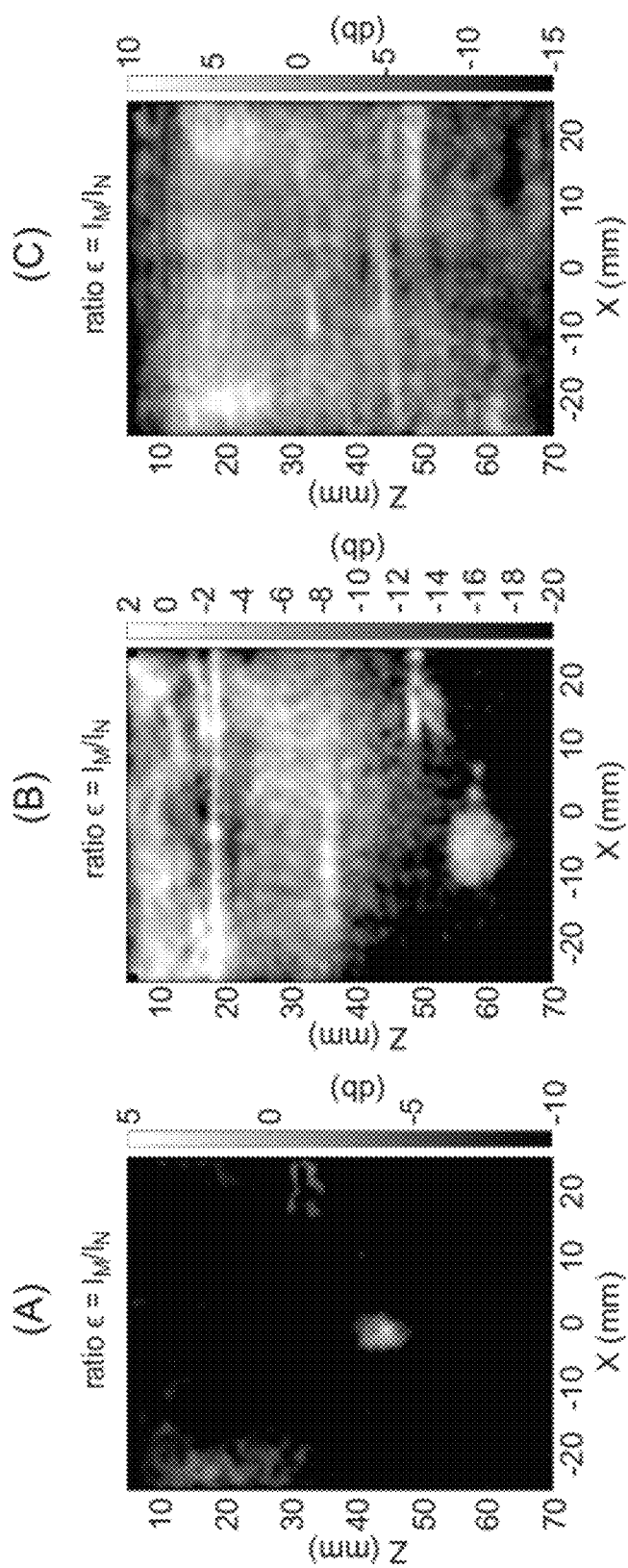
FIG. 10 illustrates images of the first multiple scattering indicator ε(r) for focusing, established for the three heterogeneous media of FIG. 7 (parts A, B, and C respectively)

FIG. 10 illustrates images of the first multiple scattering indicator ε(r) established for the three heterogeneous media of FIG. 7 (media A, B, and C, which correspond between FIGS. 7 and 10). These figures are graduated in decibels (logarithmic scale).

A large value for this first multiple scattering indicator corresponds to a high multiple scattering proportion (light in the figure). A small value for this focusing criterion corresponds to little or insignificant multiple scattering (dark in the figure). Thus, for medium A, this first multiple scattering indicator shows a localized region of ultrasonic wave scattering behind one of the heterogeneity cylinders. For media B and C, this first multiple scattering indicator highlights the scattering in most of the volume of these media, either downstream from the meat portion of medium B, or downstream from the fatty tissues of the liver.

Calculating an Afocal Intensity $I_{off}(r)$

It is then possible to carry out a step of determining an afocal intensity $I_{off}(r)$ of the central point PC, this afocal intensity being a mean of a squared modulus of the responses REP(r,Δr), the mean being calculated for distance values of modulus greater than a predetermined resolution $w_d(r)$ (i.e. $|\Delta r| > w_d(r)$) and/or calculated for a range of angle values β or for a predetermined angle value $β_d$, for example calculated by the following formula:

$$I_{off}(r) = \langle I(r,\Delta r) \rangle_{(|\Delta r| > w_d(r), \beta)} \qquad \text{(Eq. 8)}$$

with $$I(r,\Delta r) = |REP(r,\Delta r)|^2 \qquad \text{(Eq. 9)}$$

in which
I(r,Δr) is the intensity of the point, i.e. the squared modulus of the response at this point,
|·| is the modulus mathematical operator, and
⟨·⟩ is the mean mathematical operator, this operator being able to be applied according to one or more variables (for example in the above, distance coordinate values greater than a predetermined resolution and angle values β).

The afocal intensity $I_{off}(r)$ is used to characterize the incoherent energy in the ultrasound image.

The afocal intensity $I_{off}(r)$ results from the contribution of echoes originating from multiple scattering phenomena (which are reciprocal) or coming from electronic noise (which are random). It is therefore possible to subdivide the afocal intensity $I_{off}(r)$ into multiple scattering intensity and noise intensity by using the level of symmetry α(r).

Calculating a Multiple Scattering Intensity $I_M(r)$

A step of determining a multiple scattering intensity $I_M(r)$ can then be performed, this multiple scattering intensity being the product of the level of symmetry α(r) and the afocal intensity $I_{off}(r)$, i.e.:

$$I_M(r) = \alpha(r) \cdot I_{off}(r) \qquad \text{(Eq. 10)}$$

Calculating a Noise Intensity $I_N(r)$

A step of determining a noise intensity $I_N(r)$ can then be performed, this noise intensity being the product of one minus the level of symmetry α(r) and the afocal intensity $I_{off}(r)$, i.e.:

$$I_N(r) = (1-\alpha(r)) \cdot I_{off}(r) \qquad \text{(Eq. 11)}$$

such that we have the following relation:

$$I_{off}(r) = I_M(r) + I_N(r) \qquad \text{(Eq. 12)}$$

Then, the first multiple scattering indicator ε(r) can also be calculated by a ratio between the multiple scattering intensity $I_M(r)$ and the noise intensity $I_N(r)$, i.e. according to the following formula:

$$\epsilon(r) = \frac{I_M(r)}{I_N(r)} \qquad \text{(Eq. 13)}$$

The proportion of multiple scattering in the ultrasound image being low due to the antenna gain obtained by the double focusing process, this indicator makes it possible to identify the regions in which the multiple scattering proportion in the ultrasound image becomes predominant over the electronic noise.

For example, for the images of FIG. 10, obtained with an angle β of zero (β=0), the following observations can be made.

In image A of FIG. 10, one can see that the increase in scatterer density in the disc (located at spatial position [X,Z]=[−5,40] mm) highlights an increase in the first multiple scattering indicator ε(r). Note that this appears for a depth greater than that of the disc. This phenomenon arises from the fact that the echoes resulting from multiple scattering phenomena have a time-of-flight which is no longer proportional to the depth of the last scatterer having interacted with the multiply-scattered wave. Consequently, this criterion makes it possible to probe the multiple scattering which takes place upstream of the point considered.

In image B of FIG. 10, at a depth Z of 38 mm, the image of the first multiple scattering indicator ε(r) shows a sharp increase in this first multiple scattering indicator. These signals arise from a double reflection of the echoes between the surface of the Phantom and the surface of the probe, which is parallel.

In image C of FIG. 10, there is a lateral pattern that repeats axially. This phenomenon arises from echoes which have been successively reflected between two parallel walls of tissue.

Calculating a Confocal Intensity $I_{on}(r)$

A step of determining a confocal intensity $I_{on}(r)$ can then be performed, this confocal intensity then being the value of a squared modulus of the response REP(r, $\Delta r=0$) for a distance coordinate value $\Delta r$ of zero, i.e. $|\Delta r|=0$, meaning for a point in the medium for which the first point P1, the second point P2, and the central point PC are coincident.

Calculating a Single Scattering Intensity $I_S(r)$

A step of determining a single scattering intensity $I_S(r)$ can then be performed, this single scattering intensity being calculated based on the following equation:

$$I_{on}(r) = I_S(r) + 2I_M(r) + I_N(r) \tag{Eq. 14}$$

Note that the factor of 2 in this equation comes from the phenomenon of coherent backscattering.

Calculating a Second Multiple Scattering Indicator $\gamma(r)$

A step of determining a second multiple scattering indicator $\gamma(r)$ can then be performed, this second multiple scattering indicator being calculated by the following formula:

$$\gamma(r) = \frac{I_M(r)}{I_S(r)} \tag{Eq. 15}$$

Figure 11:
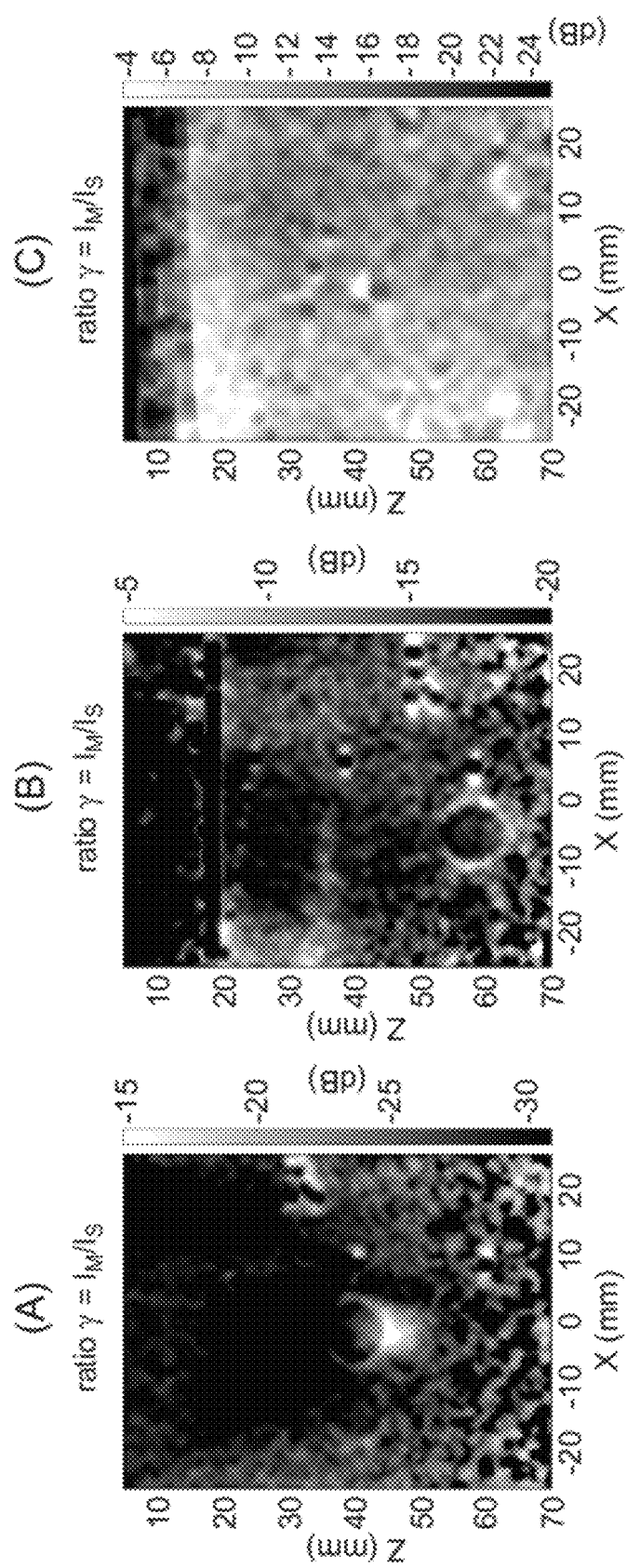
FIG. 11 illustrates images of the second multiple scattering indicator γ(r) established for the three heterogeneous media of FIG. 7 (parts A, B, and C respectively)

This second multiple scattering indicator $\gamma(r)$ makes it possible to compare the proportion of multiple scattering to the proportion of single scattering. FIG. 11 illustrates images of the second multiple scattering indicator $\gamma(r)$ established for the three heterogeneous media of FIG. 7 (media A, B, and C, which correspond between FIGS. 7 and 10). These figures are graduated in decibels (logarithmic scale).

A large value for this first multiple scattering indicator corresponds to a large proportion of multiple scattering compared to single scattering (light in the figure). A low value for this second multiple scattering indicator corresponds to little multiple scattering compared to single scattering (dark in the figure). Thus, this second multiple scattering indicator shows that medium C is highly scattering.

Although the images of FIG. 11 highlight the same phenomena observed in the corresponding images of FIG. 10 but with a different contrast, this second multiple scattering indicator makes it possible to determine a new criterion sensitive to the phenomenon of multiple scattering, independently of the attenuation of the medium. In effect, we are studying the echoes which have the same propagation time inside the medium: they therefore have been attenuated in the same manner.

Optimizing the Ultrasound Image Calculation

One possible use of the above calculations is to optimize the calculation of the ultrasound image.

The ultrasound image is for example calculated by successive input and output focusing for all points in the medium. The set of points on the abscissa axis of FIG. 5 corresponds to a row of this ultrasound image calculated at the depth z used to form the image of this FIG. 5.

However, this ultrasound image calculation strongly depends on the assumption of a homogeneous medium in which the speed of sound (the speed of propagation of ultrasonic waves) is well-known and constant. If this assumption is incorrect, the focusing delay rules do not correspond to the medium considered and the focusing is imperfect. The resolution of the ultrasound image is then degraded. Other focusing calculation parameters may possibly influence focusing.

An image optimization step can then be carried out in which the focusing criterion F(r) is calculated at a plurality of points in the medium (for example a predetermined region of the image), and at least one calculation parameter for the input focusing and/or output focusing is optimized by minimizing or maximizing a mean of said focusing criterion F(r) for said plurality of points.

For example, said at least one calculation parameter comprises at least the speed of sound in the medium. Optionally, this calculation parameter is the speed of sound.

Figure 12:
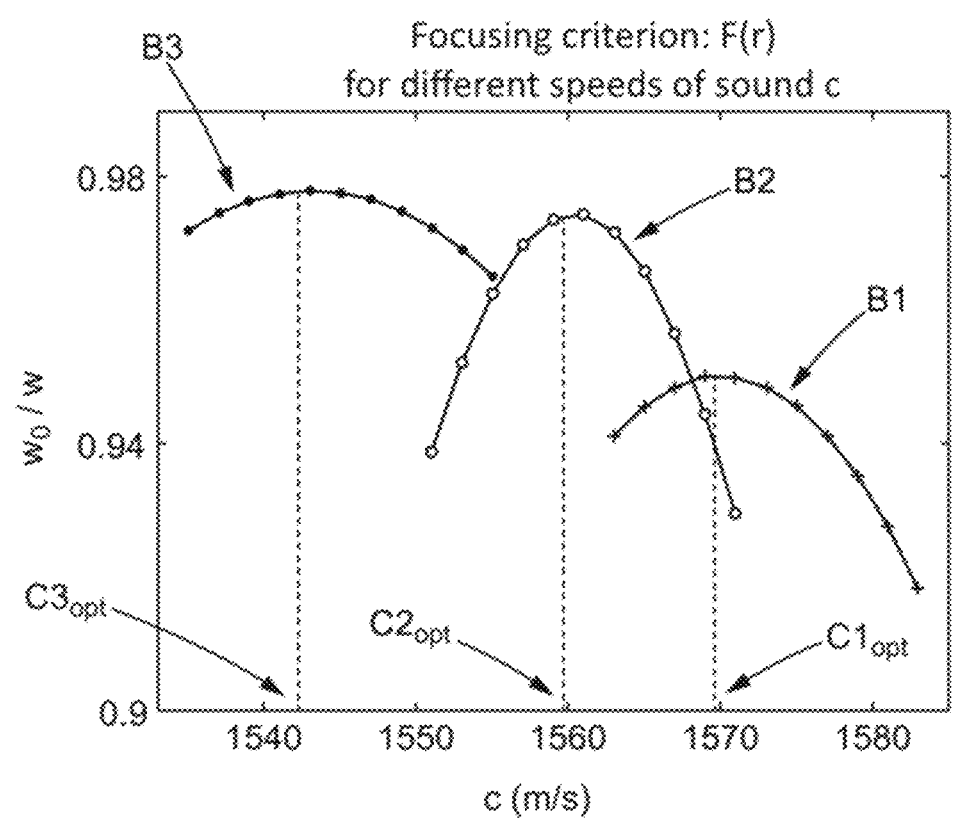
FIG. 12 illustrates three calculations of optimal speeds of sound, carried out based on three models of medium B of FIG. 7 and based on the defined focusing criterion F(r).

In the case of optimizing the focusing criterion F(r) based on a possible range of the speed of sound c, a curve is obtained similar to one of those presented in FIG. 12, and for which the focusing criterion F(r) exhibits a maximum for an optimum speed of sound $c_{opt}$. This optimum speed of sound $c_{opt}$ corresponds in fact to a speed of sound integrated over the entire thickness of the medium traversed (between the probe and the focal plane of the predetermined region).

In other words, the focus quality and therefore the focusing criterion is maximal when the speed of sound model used to carry out the focusing coincides with the true speed of sound of the medium.

To improve the estimation of the speed of sound in the medium, it is necessary for example to introduce a multilayered model of the medium, each layer being assumed to be homogeneous with a speed of sound $c_i$ of this layer. The thickness of each layer must be estimated, either with prior knowledge of the medium, or based on a first ultrasound image. By optimization of the focusing criterion, one therefore estimates the speed of sound in the outermost layer with a homogeneous model, then by optimization the next layer one estimates the speed of sound in the next layer with a two-layer model, and so on.

FIG. 12 illustrates the optimizations carried out for a same predetermined region of medium B, using:

a) a single-layer model in curve B1 with optimum speed of sound $c1_{opt}$,
b) a two-layer model in curve B2 with optimum speed of sound $c2_{opt}$,
c) a three-layer model in curve B1 with optimum speed of sound $c3_{opt}$, The optimization method presented above and the multilayer modeling of the medium therefore make it possible to refine the speed of sound estimates, and therefore make it possible to determine the depthwise evolution of the speed of sound in the medium.

The invention claimed is:

1. Method for non-invasive ultrasound characterization of a heterogeneous medium, the method comprising:
   generating a series of incident ultrasonic waves in a region of the heterogeneous medium, generated by a transducer array, said series of incident ultrasonic waves constituting an input emission basis (i);
   recording an experimental reflection matrix $R_{ui}(t)$ defined between the input emission basis (i) and an output reception basis (u);
   determining a response REP(r,$\Delta r$) of the medium between an input virtual transducer ($TV_{in}$) of spatial position $r_{in}$ calculated based on an input focusing of the experimental reflection matrix corresponding to an input focal spot around a first point (P1) and an output virtual transducer ($TV_{out}$) of spatial position $r_{out}$ calculated based on an output focusing of the experimental reflection matrix corresponding to an output focal spot around a second point (P2), said response REP(r,Δr) being expressed as a function of a central point (PC) of spatial position r in the medium and as a function of a distance coordinate Δr from said central point, said central point (PC) being located midway between the first and second points (P1, P2) such that $r=(r_{out}+r_{in})/2$ and such that $\Delta r=(r_{out}-r_{in})/2$, and said central point being the origin of a measurement axis (AXm) passing through said first and second points (P1, P2), said measurement axis (AXm) forming an angle β relative to a first axis (X) of the medium, and the first point (P1) being at the distance coordinate +Δr on the measurement axis (AXm), and the second point (P2) being at an opposite distance coordinate −Δr on the measurement axis (AXm).

2. Method according to claim 1, wherein, in determining the response REP(r,Δr), the input focusing of the experimental reflection matrix uses an outward time-of-flight of the waves between the input emission basis and the input virtual transducer, and the output focusing uses a return time-of-flight of the waves between the output virtual transducer and the output reception basis.

3. Method according to claim 1, wherein the response REP(r,Δr) of the medium is calculated by the following formula:

$$REP(r, \Delta r) = \frac{1}{N_{in}N_{out}}\sum_{i_{in}}\sum_{u_{out}} R_{ui}(u_{out}, i_{in}, \tau(r_{in}, r_{out}, u_{out}, i_{in}))$$

in which $N_{in}$ is the number of elements of the input emission basis, $N_{out}$ is the number of elements of the output reception basis, $R_{ui}(t)$ is the experimental reflection matrix, in which $R_{ui}(u_{out}, i_{in}, \tau(r_{in}, r_{out}, u_{out}, i_{in}))$ is the element of the experimental reflection matrix $R_{ui}(t)$ recorded by transducer $u_{out}$ consecutive to emission $i_{in}$ at time τ, τ is a time which is the sum of the outward time-of-flight $\tau_{in}$ of the ultrasonic wave between the input emission basis (i) and the first point (P1) and the return time-of-flight Tout of the ultrasonic wave between the second point (P2) and the output reception basis (u), as explained by the following formula:

$$\tau(r_{in},r_{out},u_{out},i_{in})=\tau_{in}(r_{in},i_{in})+\tau_{out}(r_{out},u_{out}).$$

4. Method according to claim 1, further comprising:
determining a response profile PR(δr) which is a plurality of responses REP(r,Δr) calculated for a plurality of values of the distance coordinate Δr and for the central point (PC), and for the measurement axis ($AX_m$), corresponding to the angle β, δr being the distance of the second point from the central point, wherein the value of said distance being such that $\Delta r=u_\beta \cdot u_\beta$, $u_\beta$ being a unit vector in the direction of the measurement axis $AX_m$ defined by the angle β.

5. Method according to claim 4, further comprising:
determining the resolution w(r) of the central point (PC) based on a modulus of the response profile PR(δr), in which the resolution w(r) is a width of a peak of said modulus of the response profile PR(δr), centered around a distance being null (δr=0).

6. Method according to claim 5, wherein the width of the peak is estimated at a height which is a portion of a maximum height of said peak, said portion being half the maximum height of the peak.

7. Method according to claim 5, further comprising:
determining a focusing criterion F(r) of the central point (PC) based on a resolution w(r) and a theoretical resolution $w_0(r)$, said theoretical resolution $w_0(r)$ being determined based on the input emission basis (i) and the output reception basis (u).

8. Method according to claim 7, further comprising:
calculating the focusing criterion F(r) at a plurality of points in the medium, and at least one calculation parameter for the input focusing and/or output focusing is optimized by minimizing or maximizing a mean of said focusing criterion F(r) for said plurality of points.

9. Method according to claim 8, wherein said at least one calculation parameter comprises the speed of sound in the medium.

10. Method according to claim 7, wherein the theoretical resolution is determined by a technique comprised in the list comprised in:
a first analytical calculation at the central point (PC), for a pulse ($\omega_1$) and the input emission basis (i) and the output reception basis (u), in which the theoretical resolution is calculated by the angle from which the transducer array is viewed from the central point (PC),
a second analytical calculation at the central point (PC), for a pulse range (Δω) and the input emission basis (i) and the output reception basis (u), in which the theoretical resolution is an integral calculation over said pulse range of the angle from which the transducer array is viewed from the central point (PC) weighted by the frequency spectrum of signals from the experimental reflection matrix $R_{ui}(t)$, and
a third calculation of wave propagation simulation, firstly between the first point of the medium corresponding to an input virtual transducer ($TV_{in}$) and the input emission basis (i), and secondly between the second point of the medium corresponding to an output virtual transducer ($TV_{out}$) and the output reception basis (u), said simulation using the response REP(r,Δr) and a model of wave propagation in the medium.

11. Method according to claim 1, further comprising:
determining a level of symmetry α(r) which is the mean correlation coefficient between two reciprocal responses, said mean being calculated for distance coordinate values of modulus greater than a predetermined resolution $w_d(r)$ and/or being calculated for a range of angle values β or for a predetermined angle value $β_d$, determining a first response REP1(r,Δr) of the medium between an input virtual transducer ($TV_{in}$) of spatial position $r_{in}$ calculated based on an input focusing of the experimental reflection matrix corresponding to an input focal spot around a first point (P1) and an output virtual transducer ($TV_{out}$) of spatial position $r_{out}$ calculated based on an output focusing of the experimental reflection matrix corresponding to an output focal spot around a second point (P2), and determining a second response REP2(r,−Δr) of the medium between an input virtual transducer ($TV_{in}$) of spatial position $r_{in}$ calculated based on an input focusing of the experimental reflection matrix corresponding to an input focal spot around the second point (P2) and an output virtual transducer ($TV_{out}$) of spatial position $r_{out}$ calculated based on an output focusing of the experimental reflection matrix corresponding to an output focal spot around the first point (P1).

12. Method according to claim 11, wherein the level of symmetry is calculated by the following formula:

$$\alpha(r) = \frac{\langle REP1(r, \Delta r) \cdot REP2(r, -\Delta r)^* \rangle_{(|\Delta r|>w_d(r,\beta),\beta)}}{\sqrt{\langle |REP1(r, \Delta r)|^2 \rangle \langle |REP2(r, -\Delta r)|^2 \rangle}}$$

or by the following formula:

$$\alpha(r) = \frac{\langle Re[REP1(r, \Delta r) \cdot REP2(r, -\Delta r)^*] \rangle_{(|\Delta r|>w_d(r,\beta),\beta)}}{\sqrt{\langle |REP1(r, \Delta r)|^2 \rangle \langle |REP2(r, -\Delta r)|^2 \rangle}}$$

in which
Re is a real part mathematical operator,
$|\cdot|$ is a modulus mathematical operator,
$\langle\cdot\rangle$ is a mean mathematical operator, and
* is a complex conjugation operator.

13. Method according to claim 11, further comprising:
determining a first multiple scattering indicator $\varepsilon(r)$ which is calculated by:

$$\varepsilon(r) = \frac{\alpha(r)}{1 - \alpha(r)}$$

$\alpha(r)$ being the level of symmetry defined at the central point (PC) of the medium.

14. Method according to claim 11, further comprising:
determining an afocal intensity $I_{off}(r)$ which is the mean of a squared modulus of the responses REP(r,$\Delta$r), the mean being calculated for distance values of modulus greater than a predetermined resolution $w_d(r)$ and/or being calculated for a range of angle values $\beta$ or for the predetermined angle value $\beta_d$, for example calculated by the following formula:

$$I_{off}(r) = \langle I_{off}(r,\Delta r) \rangle_{(|\Delta r|>w_d(r))}$$

determining a multiple scattering intensity $I_M(r)$ which is the product of the level of symmetry $\alpha(r)$ and the afocal intensity $I_{off}(r)$, wherein:

$$I_M(r) = \alpha(r) \cdot I_{off}(r)$$

determining a noise intensity $I_N(r)$ being the product of one minus the level of symmetry $\alpha(r)$ and the afocal intensity $I_{off}(r)$, wherein:

$$I_N(r) = (1-\alpha(r)) \cdot I_{off}(r).$$

15. Method according to claim 14, wherein the first multiple scattering indicator $\varepsilon(r)$ is calculated by a ratio between the multiple scattering intensity $I_M(r)$ and the noise intensity $I_N(r)$, wherein:

$$\varepsilon(r) = \frac{I_M(r)}{I_N(r)}.$$

16. Method according to claim 14, further comprising:
determining a confocal intensity $I_{on}(r)$ which is the value of a squared modulus of the response REP(r, $|\Delta r|=0$) for a distance coordinate value of zero ($|\Delta r|=0$), wherein for a point of the medium for which the first point (P1), the second point (P2), and the central point (PC) are coincident,
determining a single scattering intensity $I_S(r)$ calculated based on the following equation:

$$I_{on}(r) = I_S(r) + 2I_M(r) + I_N(r).$$

17. Method according to claim 14, further comprising:
determining a second multiple scattering indicator $\gamma(r)$ which is calculated by:

$$\gamma(r) = \frac{I_M(r)}{I_S(r)}.$$

18. Method according to claim 1, further comprising:
determining an image of a local characterization parameter of the medium, said local characterization parameter being determined based on the response REP(r,$\Delta$r).

19. System for non-invasive ultrasonic characterization of a heterogeneous medium, the system comprising:
a first array of transducers suitable for generating a series of incident ultrasonic waves in a region of the heterogeneous medium, said series of incident ultrasonic waves constituting an input emission basis (i), and suitable for recording as a function of time the ultrasonic waves backscattered by said region; and
a computing unit coupled to the first array of transducers and configured for:
recording an experimental reflection matrix $R_{ui}(t)$ defined between the input emission basis (i) and an output reception basis (u);
determining a response REP(r,$\Delta$r) of the medium between an input virtual transducer ($TV_{in}$) of spatial position $r_{in}$ calculated based on an input focusing of the experimental reflection matrix corresponding to an input focal spot around a first point (P1) and an output virtual transducer ($TV_{out}$) of spatial position $r_{out}$ calculated based on an output focusing of the experimental reflection matrix corresponding to an output focal spot around a second point (P2),
said response REP(r,$\Delta$r) being expressed as a function of a central point (PC) of spatial position r in the medium and as a function of a distance coordinate $\Delta$r from said central point,
said central point (PC) being located midway between the first and second points (P1, P2) such that $r=(r_{out}+r_{in})/2$ and such that $\Delta r=(r_{out}-r_{in})/2$, and
said central point (PC) being the origin of a measurement axis ($AX_m$) passing through said first and second point s (P1, P2), said measurement axis ($AX_m$) forming an angle $\beta$ relative to a first axis (X) of the medium, and
the first point (P1) being at the distance coordinate +$\Delta$r on the measurement axis (AXm), and the second point (P2) being at an opposite distance coordinate $-\Delta$r on the measurement axis (AXm).

* * * * *

UNITED STATES PATENT AND TRADEMARK OFFICE
CERTIFICATE OF CORRECTION

PATENT NO. : 12,257,103 B2
APPLICATION NO. : 17/631929
DATED : March 25, 2025
INVENTOR(S) : William Lambert et al.

Page 1 of 1

It is certified that error appears in the above-identified patent and that said Letters Patent is hereby corrected as shown below:

In the Specification

Column 4, Line 16, "matrix IWO" should read -- matrix $R_{ui}(t)$ --.

Column 18, Line 34, "value $\Delta d$." should read -- value $\beta_d$. --.

In the Claims

Claim 3, Column 23, Line 47, "of-flight Tout" should read -- of-flight $T_{out}$ --.

Claim 4, Column 23, Line 59, "$\Delta r = u_\beta.u_\beta, u_\beta$" should read -- $\Delta r = \delta r.u_\beta, u_\beta$ --.

Claim 14, Column 25, Line 41, "$I_{off}(r) = \langle I_{off}(r, \Delta r) \rangle_{(|\Delta r| > w_d(r))}$" should read -- $I_{off}(r) = \langle I(r, \Delta r) \rangle_{(|\Delta r| > w_d(r))}$ --.

Claim 19, Column 26, Line 54, "point s" should read -- points --.

Signed and Sealed this
Twenty-fourth Day of June, 2025

Coke Morgan Stewart
*Acting Director of the United States Patent and Trademark Office*